(12) United States Patent
Paniagua et al.

(10) Patent No.: US 8,790,398 B2
(45) Date of Patent: Jul. 29, 2014

(54) PERCUTANEOUSLY IMPLANTABLE REPLACEMENT HEART VALVE DEVICE AND METHOD OF MAKING SAME

(71) Applicant: Colibri Heart Valve LLC, Broomfield, CO (US)

(72) Inventors: David Paniagua, Houston, TX (US); R. David Fish, Houston, TX (US)

(73) Assignee: Colibri Heart Valve LLC, Broomfield, CO (US)

( * ) Notice: Subject to any disclaimer, the term of this patent is extended or adjusted under 35 U.S.C. 154(b) by 0 days.

(21) Appl. No.: 14/136,516

(22) Filed: Dec. 20, 2013

(65) Prior Publication Data

US 2014/0114395 A1    Apr. 24, 2014

Related U.S. Application Data

(63) Continuation of application No. 13/672,665, filed on Nov. 13, 2012, which is a continuation of application No. 10/887,688, filed on Jul. 10, 2004, now Pat. No. 8,308,797, which is a continuation-in-part of application No. 10/037,266, filed on Jan. 4, 2002, now abandoned.

(51) Int. Cl.
*A61F 2/24* (2006.01)

(52) U.S. Cl.
CPC ............. *A61F 2/2412* (2013.01); *A61F 2/24* (2013.01); *A61F 2/2475* (2013.01); *A61F 2250/0039* (2013.01)
USPC .......... 623/2.18; 623/1.3; 623/2.13; 623/1.24

(58) Field of Classification Search
CPC ........ A61F 2/24; A61F 2/2412; A61F 2/2475
USPC ...................... 623/1.24, 1.26, 2.12–2.19, 900
See application file for complete search history.

(56) References Cited

U.S. PATENT DOCUMENTS

| 3,014,024 A | 12/1961 | Lieberman et al. |
| 3,029,819 A | 4/1962 | Edward |

(Continued)

FOREIGN PATENT DOCUMENTS

| EP | 1603493 | 12/2005 |
| EP | 2000115 | 5/2011 |

(Continued)

OTHER PUBLICATIONS

Pathak, CP et al., "Treatment of bioprosthetic heart valve tissue with long chain alcohol solution to lower calcification potential" J Biomed Mater Res A. Apr. 1, 2004;69(1):140-4.

(Continued)

*Primary Examiner* — Thomas J Sweet
*Assistant Examiner* — Cheryl Miller
(74) *Attorney, Agent, or Firm* — Fox Rothschild LLP

(57) ABSTRACT

A method of making a replacement heart valve device whereby a fragment of biocompatible tissue material is treated and soaked in one or more alcohol solutions and a solution of glutaraldehyde. The dried biocompatible tissue material is folded and rehydrated in such a way that forms a two- or three-leaflet/cusp valve without affixing of separate cusps or leaflets or cutting slits into the biocompatible tissue material to form the cusps or leaflets. After the biocompatible tissue material is folded, it is affixed at one or more points on the outer surface to the inner cavity or a stent.

5 Claims, 12 Drawing Sheets

(56) References Cited

U.S. PATENT DOCUMENTS

| | | |
|---|---|---|
| 3,105,492 A | 10/1963 | Jeckel |
| 3,320,972 A | 5/1967 | High et al. |
| 3,409,914 A | 11/1968 | Jones |
| 3,548,417 A | 12/1970 | Kischer et al. |
| 3,562,820 A | 2/1971 | Braun |
| 3,588,920 A | 6/1971 | Wesolowski |
| 3,671,979 A | 6/1972 | Moulopoulos |
| 3,709,175 A | 1/1973 | Edwards et al. |
| 3,878,565 A | 4/1975 | Sauvage |
| 3,945,052 A | 3/1976 | Liebig |
| 3,966,401 A | 6/1976 | Hancock et al. |
| 3,983,581 A | 10/1976 | Angell et al. |
| 3,986,828 A | 10/1976 | Hoffman, Jr. et al. |
| 4,035,849 A | 7/1977 | Angell et al. |
| 4,055,861 A | 11/1977 | Carpentier et al. |
| 4,056,854 A | 11/1977 | Boretos et al. |
| 4,060,081 A | 11/1977 | Yannas et al. |
| 4,082,507 A | 4/1978 | Sawyer |
| 4,084,268 A | 4/1978 | Ionescu et al. |
| 4,106,129 A | 8/1978 | Carpentier et al. |
| 4,164,045 A | 8/1979 | Bokros et al. |
| 4,172,295 A | 10/1979 | Batten |
| 4,218,782 A | 8/1980 | Rygg |
| 4,222,126 A | 9/1980 | Boretos et al. |
| 4,233,493 A | 11/1980 | Nath et al. |
| 4,265,694 A | 5/1981 | Boretos et al. |
| 4,291,420 A | 9/1981 | Reul |
| 4,340,977 A | 7/1982 | Brownlee et al. |
| 4,350,492 A | 9/1982 | Wright et al. |
| 4,364,127 A | 12/1982 | Pierce et al. |
| 4,388,735 A | 6/1983 | Ionescu et al. |
| 4,423,525 A | 1/1984 | Vallana et al. |
| 4,441,216 A | 4/1984 | Ionescu et al. |
| 4,456,589 A | 6/1984 | Holman et al. |
| 4,473,423 A | 9/1984 | Kolff |
| 4,477,930 A | 10/1984 | Totten et al. |
| 4,490,859 A | 1/1985 | Black et al. |
| 4,517,687 A | 5/1985 | Liebig et al. |
| 4,545,082 A | 10/1985 | Hood |
| 4,597,762 A | 7/1986 | Walter et al. |
| 4,600,533 A | 7/1986 | Chu |
| 4,631,052 A | 12/1986 | Kensey |
| 4,666,442 A | 5/1987 | Arru et al. |
| 4,728,328 A | 3/1988 | Hughes et al. |
| 4,759,758 A | 7/1988 | Gabbay |
| 4,759,759 A | 7/1988 | Walker et al. |
| 4,798,611 A | 1/1989 | Freeman, Jr. |
| 4,801,299 A | 1/1989 | Brendel et al. |
| 4,870,966 A | 10/1989 | Dellon et al. |
| 4,883,458 A | 11/1989 | Shiber |
| 4,892,539 A | 1/1990 | Koch |
| 4,966,604 A | 10/1990 | Reiss |
| 4,976,733 A | 12/1990 | Giradot |
| 4,979,939 A | 12/1990 | Shiber |
| 5,006,104 A | 4/1991 | Smith et al. |
| 5,007,896 A | 4/1991 | Shiber |
| 5,011,488 A | 4/1991 | Ginsburg |
| 5,026,366 A | 6/1991 | Leckrone |
| 5,032,128 A | 7/1991 | Alonso |
| 5,047,041 A | 9/1991 | Samuels |
| 5,047,050 A | 9/1991 | Arpesani |
| 5,052,771 A | 10/1991 | Williams et al. |
| 5,061,277 A | 10/1991 | Carpentier et al. |
| 5,080,660 A | 1/1992 | Buelna |
| 5,139,515 A | 8/1992 | Robicsek |
| 5,163,955 A | 11/1992 | Love et al. |
| 5,171,273 A | 12/1992 | Silver et al. |
| 5,226,889 A | 7/1993 | Sheiban |
| 5,261,878 A | 11/1993 | Galindo |
| 5,282,847 A | 2/1994 | Trescony et al. |
| 5,326,370 A | 7/1994 | Love et al. |
| 5,326,371 A | 7/1994 | Love et al. |
| 5,332,402 A | 7/1994 | Teitelbaum |
| 5,336,616 A | 8/1994 | Livesey et al. |
| 5,360,443 A | 11/1994 | Barone et al. |
| 5,374,539 A | 12/1994 | Nimni et al. |
| 5,376,110 A | 12/1994 | Tu et al. |
| 5,383,927 A | 1/1995 | De Goiceochea et al. |
| 5,411,552 A | 5/1995 | Anderson et al. |
| 5,413,601 A | 5/1995 | Keshelava |
| 5,449,384 A | 9/1995 | Johnson |
| 5,476,506 A | 12/1995 | Lunn |
| 5,480,424 A | 1/1996 | Cox |
| 5,489,297 A | 2/1996 | Duran |
| 5,500,015 A | 3/1996 | Deac |
| 5,509,930 A * | 4/1996 | Love ............... 623/2.1 |
| 5,522,879 A | 6/1996 | Scopelianos |
| 5,522,881 A | 6/1996 | Lentz |
| 5,545,215 A | 8/1996 | Duran |
| 5,549,664 A | 8/1996 | Hirata et al. |
| 5,549,666 A | 8/1996 | Hata et al. |
| 5,571,170 A | 11/1996 | Palmaz et al. |
| 5,571,173 A | 11/1996 | Parodi |
| 5,571,174 A | 11/1996 | Love et al. |
| 5,578,071 A | 11/1996 | Parodi |
| 5,578,072 A | 11/1996 | Barone et al. |
| 5,582,168 A | 12/1996 | Samuels et al. |
| 5,591,229 A | 1/1997 | Parodi |
| 5,634,928 A | 6/1997 | Fischell et al. |
| 5,653,749 A | 8/1997 | Love et al. |
| 5,713,953 A | 2/1998 | Vallana et al. |
| 5,728,152 A | 3/1998 | Mirsch, II et al. |
| 5,733,299 A | 3/1998 | Sheiban et al. |
| 5,741,333 A | 4/1998 | Frid |
| 5,746,775 A | 5/1998 | Levy et al. |
| 5,769,780 A | 6/1998 | Hata et al. |
| 5,782,914 A | 7/1998 | Schankerel |
| 5,787,887 A | 8/1998 | Klingenbeck-Regn |
| 5,840,081 A | 11/1998 | Anderson et al. |
| 5,855,601 A | 1/1999 | Bessler et al. |
| 5,861,028 A | 1/1999 | Angell |
| 5,862,806 A | 1/1999 | Cheung |
| 5,895,420 A | 4/1999 | Mirsch, II et al. |
| 5,931,969 A | 8/1999 | Carpentier et al. |
| 5,957,949 A | 9/1999 | Leonhardt et al. |
| 5,961,539 A | 10/1999 | Northrup et al. |
| 5,961,549 A | 10/1999 | Nguyen et al. |
| 5,972,030 A | 10/1999 | Garrison et al. |
| 5,976,179 A | 11/1999 | Inoue |
| 6,004,328 A | 12/1999 | Solar |
| 6,004,330 A | 12/1999 | Middleman et al. |
| 6,010,531 A | 1/2000 | Donlon et al. |
| 6,029,671 A | 2/2000 | Stevens et al. |
| 6,045,576 A | 4/2000 | Starr et al. |
| 6,053,938 A | 4/2000 | Goldmann et al. |
| 6,091,984 A | 7/2000 | Perelman et al. |
| 6,102,944 A | 8/2000 | Huynh et al. |
| 6,117,169 A | 9/2000 | Moe |
| 6,124,523 A * | 9/2000 | Banas et al. ............... 623/1.15 |
| 6,125,852 A | 10/2000 | Stevens et al. |
| 6,126,686 A | 10/2000 | Badylak et al. |
| 6,129,756 A | 10/2000 | Kugler |
| 6,162,245 A | 12/2000 | Jayaraman |
| 6,168,614 B1 | 1/2001 | Andersen et al. |
| 6,168,619 B1 | 1/2001 | Dinh et al. |
| 6,171,335 B1 | 1/2001 | Wheatley et al. |
| 6,174,327 B1 | 1/2001 | Mertens et al. |
| 6,186,999 B1 | 2/2001 | Chen |
| 6,197,143 B1 | 3/2001 | Bodnar |
| 6,214,055 B1 | 4/2001 | Simionescu et al. |
| 6,221,091 B1 | 4/2001 | Khosravi |
| 6,231,602 B1 | 5/2001 | Carpentier et al. |
| 6,245,102 B1 * | 6/2001 | Jayaraman ............... 623/1.15 |
| 6,254,629 B1 | 7/2001 | Inoue |
| 6,254,630 B1 | 7/2001 | Inoue |
| 6,254,636 B1 | 7/2001 | Peredo |
| 6,264,691 B1 | 7/2001 | Gabbay |
| 6,269,819 B1 | 8/2001 | Oz et al. |
| 6,270,526 B1 | 8/2001 | Cox |
| 6,277,397 B1 | 8/2001 | Shimizu |
| 6,277,555 B1 | 8/2001 | Duran et al. |
| 6,287,335 B1 | 9/2001 | Drasler et al. |
| 6,293,970 B1 | 9/2001 | Wolfinbarger, Jr. et al. |
| 6,312,462 B1 | 11/2001 | McDermott et al. |

(56) References Cited

U.S. PATENT DOCUMENTS

| | | |
|---|---|---|
| 6,312,474 B1 | 11/2001 | Francis et al. |
| 6,334,873 B1 | 1/2002 | Lane et al. |
| 6,342,069 B1 | 1/2002 | Deac et al. |
| 6,350,282 B1 | 2/2002 | Eberhardt |
| 6,352,554 B2 | 3/2002 | De Paulis |
| 6,352,708 B1 | 3/2002 | Duran et al. |
| 6,358,275 B1 | 3/2002 | McIlroy et al. |
| 6,358,284 B1 | 3/2002 | Fearnot et al. |
| 6,371,980 B1 | 4/2002 | Rudakov et al. |
| 6,376,244 B1 | 4/2002 | Atala et al. |
| 6,378,221 B1 | 4/2002 | Ekholm, Jr. et al. |
| 6,383,171 B1 | 5/2002 | Gifford et al. |
| 6,391,333 B1 | 5/2002 | Li et al. |
| 6,409,755 B1 | 6/2002 | Vrba |
| 6,418,339 B1 | 7/2002 | Essenpreis et al. |
| 6,425,916 B1 | 7/2002 | Garrison et al. |
| 6,432,712 B1 | 8/2002 | Wolfinbarger, Jr. et al. |
| 6,440,167 B2 | 8/2002 | Shimizu |
| 6,458,153 B1 * | 10/2002 | Bailey et al. ............... 623/1.24 |
| 6,461,382 B1 | 10/2002 | Cao |
| 6,468,313 B1 | 10/2002 | Claeson et al. |
| 6,471,723 B1 | 10/2002 | Ashworth et al. |
| 6,482,227 B1 | 11/2002 | Solovay |
| 6,482,228 B1 | 11/2002 | Norred |
| 6,482,240 B1 | 11/2002 | Eckmayer et al. |
| 6,491,719 B1 | 12/2002 | Fogarty et al. |
| 6,494,909 B2 | 12/2002 | Greenhalgh |
| 6,503,272 B2 | 1/2003 | Duerig et al. |
| 6,534,004 B2 | 3/2003 | Chen et al. |
| 6,553,681 B2 | 4/2003 | Ekholm, Jr. et al. |
| 6,558,418 B2 | 5/2003 | Carpentier et al. |
| 6,565,960 B2 | 5/2003 | Koob et al. |
| 6,569,200 B2 | 5/2003 | Wolfinbarger, Jr. et al. |
| 6,582,458 B1 | 6/2003 | White et al. |
| 6,582,462 B1 | 6/2003 | Andersen et al. |
| 6,582,464 B2 | 6/2003 | Gabbay |
| 6,599,524 B2 | 7/2003 | Li et al. |
| 6,610,088 B1 | 8/2003 | Gabbay |
| 6,624,890 B2 | 9/2003 | Backman et al. |
| 6,626,938 B1 | 9/2003 | Butaric et al. |
| 6,652,577 B2 | 11/2003 | Gianotti |
| 6,652,578 B2 | 11/2003 | Bailey et al. |
| 6,666,886 B1 | 12/2003 | Tranquillo et al. |
| 6,682,559 B2 | 1/2004 | Myers et al. |
| 6,685,739 B2 | 2/2004 | Dimatteo et al. |
| 6,696,074 B2 | 2/2004 | Dai et al. |
| 6,702,826 B2 | 3/2004 | Liddicoat et al. |
| 6,719,788 B2 | 4/2004 | Cox |
| 6,719,789 B2 | 4/2004 | Cox |
| 6,736,823 B2 | 5/2004 | Darios et al. |
| 6,764,510 B2 | 7/2004 | Vidlund et al. |
| 6,773,456 B1 | 8/2004 | Gordon et al. |
| 6,773,457 B2 | 8/2004 | Ivancev |
| 6,790,229 B1 | 9/2004 | Berreklouw |
| 6,792,979 B2 | 9/2004 | Konya et al. |
| 6,802,319 B2 | 10/2004 | Stevens et al. |
| 6,802,806 B2 | 10/2004 | McCarthy et al. |
| 6,821,530 B2 | 11/2004 | Koob et al. |
| 6,893,460 B2 | 5/2005 | Spenser et al. |
| 6,908,481 B2 * | 6/2005 | Cribier ............... 623/2.11 |
| 6,913,608 B2 | 7/2005 | Liddicoat et al. |
| 6,916,338 B2 | 7/2005 | Speziali |
| 6,942,694 B2 | 9/2005 | Liddicoat et al. |
| 6,951,571 B1 | 10/2005 | Srivastava |
| 6,961,123 B1 | 11/2005 | Wang et al. |
| 6,977,231 B1 | 12/2005 | Matsuda |
| 6,986,735 B2 | 1/2006 | Abraham et al. |
| 7,004,925 B2 | 2/2006 | Navia et al. |
| 7,008,763 B2 | 3/2006 | Cheung |
| 7,011,688 B2 | 3/2006 | Gryska et al. |
| 7,018,404 B2 | 3/2006 | Holmberg et al. |
| 7,022,348 B2 | 4/2006 | Ketharanathan |
| 7,025,780 B2 | 4/2006 | Gabbay |
| 7,037,333 B2 | 5/2006 | Myers et al. |
| 7,039,446 B2 | 5/2006 | Ruchti et al. |
| 7,041,132 B2 | 5/2006 | Quijano et al. |
| 7,053,051 B2 | 5/2006 | Hendriks et al. |
| 7,060,092 B2 | 6/2006 | Kuribayashi et al. |
| 7,070,616 B2 | 7/2006 | Majercak et al. |
| 7,077,862 B2 | 7/2006 | Vidlund et al. |
| 7,084,082 B1 | 8/2006 | Shimizu |
| 7,138,226 B2 | 11/2006 | Vincek et al. |
| 7,153,324 B2 | 12/2006 | Case et al. |
| 7,160,322 B2 | 1/2007 | Gabbay |
| 7,164,145 B2 | 1/2007 | Shakespeare |
| 7,166,570 B2 | 1/2007 | Hunter et al. |
| 7,189,259 B2 | 3/2007 | Simionescu et al. |
| 7,213,601 B2 | 5/2007 | Stevens et al. |
| 7,214,242 B2 | 5/2007 | Abraham et al. |
| 7,232,461 B2 | 6/2007 | Ramer |
| 7,261,732 B2 | 8/2007 | Justino |
| 7,289,211 B1 | 10/2007 | Walsh, Jr. et al. |
| 7,309,461 B2 | 12/2007 | Kujawski et al. |
| 7,311,730 B2 | 12/2007 | Gabbay |
| 7,318,998 B2 | 1/2008 | Goldstein et al. |
| 7,329,279 B2 | 2/2008 | Haug et al. |
| 7,331,993 B2 | 2/2008 | White |
| 7,354,702 B2 | 4/2008 | Dai et al. |
| RE40,404 E | 6/2008 | Schmitt et al. |
| 7,381,218 B2 | 6/2008 | Schreck |
| 7,381,219 B2 | 6/2008 | Salahieh et al. |
| 7,399,315 B2 | 7/2008 | Iobbi |
| 7,427,291 B2 | 9/2008 | Liddicoat et al. |
| 7,431,725 B2 | 10/2008 | Stack et al. |
| 7,468,073 B2 | 12/2008 | Johnson et al. |
| 7,473,237 B2 | 1/2009 | Navia et al. |
| 7,481,838 B2 | 1/2009 | Carpentier et al. |
| 7,503,929 B2 | 3/2009 | Johnson et al. |
| 7,510,571 B2 | 3/2009 | Spiridigliozzi et al. |
| 7,510,575 B2 | 3/2009 | Spenser et al. |
| 7,524,330 B2 | 4/2009 | Berreklouw |
| 7,566,343 B2 | 7/2009 | Jenson et al. |
| 7,585,321 B2 | 9/2009 | Cribier |
| 7,604,661 B2 | 10/2009 | Pavcnik et al. |
| 7,618,446 B2 | 11/2009 | Andersen et al. |
| 7,622,276 B2 | 11/2009 | Cunanan et al. |
| 7,628,805 B2 | 12/2009 | Spenser et al. |
| 7,648,676 B2 | 1/2010 | Mills et al. |
| 7,670,368 B2 | 3/2010 | Hill et al. |
| 7,708,775 B2 | 5/2010 | Rowe et al. |
| 7,758,632 B2 | 7/2010 | Hojeibane et al. |
| 7,780,722 B2 | 8/2010 | Thielen et al. |
| 7,789,909 B2 | 9/2010 | Andersen et al. |
| 7,846,203 B2 | 12/2010 | Cribier |
| 7,846,204 B2 | 12/2010 | Letac et al. |
| 7,871,431 B2 | 1/2011 | Gurm et al. |
| 7,892,281 B2 | 2/2011 | Seguin et al. |
| 7,914,576 B2 | 3/2011 | Navia et al. |
| RE42,395 E | 5/2011 | Wright et al. |
| 7,967,833 B2 | 6/2011 | Sterman et al. |
| 7,981,151 B2 | 7/2011 | Rowe |
| 8,002,825 B2 | 8/2011 | Letac et al. |
| 8,007,992 B2 | 8/2011 | Tian et al. |
| 8,057,540 B2 | 11/2011 | Letac et al. |
| 8,080,054 B2 | 12/2011 | Rowe |
| 8,105,375 B2 | 1/2012 | Navia et al. |
| 2001/0010017 A1 | 7/2001 | Letac et al. |
| 2001/0023372 A1 | 9/2001 | Chen et al. |
| 2001/0049558 A1 | 12/2001 | Liddicoat et al. |
| 2002/0005073 A1 | 1/2002 | Tompkins et al. |
| 2002/0028243 A1 | 3/2002 | Masters |
| 2002/0029783 A1 | 3/2002 | Stevens et al. |
| 2002/0037940 A1 | 3/2002 | Koob et al. |
| 2002/0042621 A1 | 4/2002 | Liddicoat et al. |
| 2002/0091441 A1 | 7/2002 | Guzik |
| 2002/0095167 A1 | 7/2002 | Liddicoat et al. |
| 2002/0095994 A1 | 7/2002 | Vesely et al. |
| 2002/0123789 A1 | 9/2002 | Francis et al. |
| 2002/0128708 A1 | 9/2002 | Northrup et al. |
| 2002/0151970 A1 | 10/2002 | Garrison et al. |
| 2003/0078659 A1 | 4/2003 | Yang |
| 2003/0102000 A1 | 6/2003 | Stevens et al. |
| 2003/0130727 A1 | 7/2003 | Drasler et al. |
| 2003/0130729 A1 | 7/2003 | Paniagua et al. |

(56) References Cited

U.S. PATENT DOCUMENTS

| | | |
|---|---|---|
| 2003/0130731 A1 | 7/2003 | Vidlund et al. |
| 2003/0149477 A1* | 8/2003 | Gabbay ............... 623/2.14 |
| 2003/0153974 A1 | 8/2003 | Spenser et al. |
| 2003/0187362 A1 | 10/2003 | Murphy et al. |
| 2003/0195620 A1 | 10/2003 | Huynh et al. |
| 2003/0204023 A1 | 10/2003 | Koob et al. |
| 2003/0212460 A1 | 11/2003 | Darois et al. |
| 2003/0212462 A1 | 11/2003 | Gryska et al. |
| 2003/0217415 A1 | 11/2003 | Crouch et al. |
| 2004/0024452 A1 | 2/2004 | Kruse et al. |
| 2004/0055608 A1 | 3/2004 | Stevens et al. |
| 2004/0059418 A1 | 3/2004 | McKay et al. |
| 2004/0098092 A1 | 5/2004 | Butaric et al. |
| 2004/0193261 A1 | 9/2004 | Berreklouw |
| 2004/0243153 A1 | 12/2004 | Liddicoat et al. |
| 2004/0243229 A1 | 12/2004 | Vidlund et al. |
| 2005/0004668 A1 | 1/2005 | Aklog et al. |
| 2005/0027369 A1 | 2/2005 | Eldridge et al. |
| 2005/0043819 A1 | 2/2005 | Schmidt et al. |
| 2005/0096673 A1 | 5/2005 | Stack et al. |
| 2005/0113910 A1 | 5/2005 | Paniagua et al. |
| 2005/0137681 A1 | 6/2005 | Shoemaker et al. |
| 2005/0137682 A1* | 6/2005 | Justino ............... 623/1.24 |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159811 A1 | 7/2005 | Lane |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0187618 A1 | 8/2005 | Gabbay |
| 2005/0191248 A1 | 9/2005 | Hunter et al. |
| 2005/0228494 A1 | 10/2005 | Marquez |
| 2005/0246035 A1 | 11/2005 | Wolfinbarger, Jr. et al. |
| 2005/0247320 A1 | 11/2005 | Stack et al. |
| 2005/0267529 A1 | 12/2005 | Crockett et al. |
| 2006/0004439 A1 | 1/2006 | Spenser et al. |
| 2006/0004443 A1 | 1/2006 | Liddicoat et al. |
| 2006/0020336 A1 | 1/2006 | Liddicoat |
| 2006/0025800 A1 | 2/2006 | Suresh |
| 2006/0041306 A1 | 2/2006 | Vidlund et al. |
| 2006/0074486 A1 | 4/2006 | Liddicoat et al. |
| 2006/0089708 A1 | 4/2006 | Osse et al. |
| 2006/0111733 A1 | 5/2006 | Shriver |
| 2006/0129225 A1 | 6/2006 | Kopia et al. |
| 2006/0134079 A1 | 6/2006 | Sih et al. |
| 2006/0140916 A1 | 6/2006 | Siani-Rose et al. |
| 2006/0173475 A1 | 8/2006 | Lafontaine et al. |
| 2006/0178740 A1 | 8/2006 | Stacchino et al. |
| 2006/0190074 A1 | 8/2006 | Hill et al. |
| 2006/0193885 A1 | 8/2006 | Neethling et al. |
| 2006/0195010 A1 | 8/2006 | Arnal et al. |
| 2006/0195183 A1 | 8/2006 | Navia et al. |
| 2006/0206203 A1 | 9/2006 | Yang et al. |
| 2006/0229701 A1 | 10/2006 | Gurm et al. |
| 2006/0240063 A9 | 10/2006 | Hunter et al. |
| 2006/0240064 A9 | 10/2006 | Hunter et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0287571 A1 | 12/2006 | Gozzi et al. |
| 2006/0292125 A1 | 12/2006 | Kellar et al. |
| 2007/0010857 A1 | 1/2007 | Sugimoto et al. |
| 2007/0043431 A1 | 2/2007 | Melsheimer |
| 2007/0050014 A1 | 3/2007 | Johnson |
| 2007/0050022 A1 | 3/2007 | Vidlund et al. |
| 2007/0056346 A1 | 3/2007 | Spenser et al. |
| 2007/0060932 A1 | 3/2007 | Stack et al. |
| 2007/0100426 A1 | 5/2007 | Rudakov et al. |
| 2007/0128174 A1 | 6/2007 | Kleinsek et al. |
| 2007/0173861 A1 | 7/2007 | Strommer et al. |
| 2007/0213813 A1 | 9/2007 | Von Segessler et al. |
| 2007/0250154 A1 | 10/2007 | Greenberg et al. |
| 2007/0263226 A1 | 11/2007 | Kurtz et al. |
| 2007/0276432 A1 | 11/2007 | Stack et al. |
| 2008/0004686 A1 | 1/2008 | Hunt et al. |
| 2008/0009667 A1 | 1/2008 | Longhini et al. |
| 2008/0009940 A1 | 1/2008 | Cribier |
| 2008/0029105 A1 | 2/2008 | Stevens et al. |
| 2008/0039871 A1 | 2/2008 | Wallace et al. |
| 2008/0039926 A1 | 2/2008 | Majercak et al. |
| 2008/0058798 A1 | 3/2008 | Wallace et al. |
| 2008/0082113 A1 | 4/2008 | Bishop et al. |
| 2008/0102439 A1 | 5/2008 | Tian et al. |
| 2008/0133004 A1 | 6/2008 | White |
| 2008/0147182 A1 | 6/2008 | Righini et al. |
| 2008/0154356 A1 | 6/2008 | Obermiller et al. |
| 2008/0177381 A1 | 7/2008 | Navia et al. |
| 2008/0183280 A1 | 7/2008 | Agnew et al. |
| 2008/0183283 A1 | 7/2008 | Downing |
| 2008/0190989 A1 | 8/2008 | Crews et al. |
| 2008/0195200 A1 | 8/2008 | Vidlund et al. |
| 2008/0199843 A1 | 8/2008 | Haverich et al. |
| 2008/0200977 A1 | 8/2008 | Paul et al. |
| 2009/0030511 A1 | 1/2009 | Paniagua et al. |
| 2009/0043383 A1 | 2/2009 | McGregor et al. |
| 2009/0062907 A1 | 3/2009 | Quijano et al. |
| 2009/0112309 A1 | 4/2009 | Jaramillo et al. |
| 2009/0132032 A9 | 5/2009 | Cribier |
| 2009/0157175 A1 | 6/2009 | Benichou |
| 2009/0164005 A1 | 6/2009 | Dove et al. |
| 2009/0187241 A1 | 7/2009 | Melshemier |
| 2009/0248149 A1 | 10/2009 | Gabbay |
| 2009/0254175 A1 | 10/2009 | Quijano et al. |
| 2009/0281609 A1 | 11/2009 | Benichou et al. |
| 2010/0030259 A1 | 2/2010 | Pavcnik et al. |
| 2010/0036479 A1 | 2/2010 | Hill et al. |
| 2010/0036484 A1 | 2/2010 | Hariton et al. |
| 2010/0048987 A1 | 2/2010 | Khairkhahan |
| 2010/0049312 A1 | 2/2010 | Edoga et al. |
| 2010/0131054 A1 | 5/2010 | Tuval et al. |
| 2010/0161036 A1 | 6/2010 | Pintor et al. |
| 2010/0185277 A1 | 7/2010 | Braido et al. |
| 2010/0217382 A1 | 8/2010 | Chau et al. |
| 2010/0234878 A1 | 9/2010 | Hruska |
| 2010/0249918 A1 | 9/2010 | Zhang |
| 2010/0256749 A1 | 10/2010 | Tran et al. |
| 2010/0256751 A1 | 10/2010 | Rowe et al. |
| 2010/0312333 A1 | 12/2010 | Navia et al. |
| 2011/0004299 A1 | 1/2011 | Navia et al. |
| 2011/0015728 A1 | 1/2011 | Jimenez et al. |
| 2011/0040375 A1 | 2/2011 | Letac et al. |
| 2011/0087322 A1 | 4/2011 | Letac et al. |
| 2011/0137409 A1 | 6/2011 | Yang et al. |
| 2011/0146361 A1 | 6/2011 | Davidson et al. |
| 2011/0153009 A1 | 6/2011 | Navia et al. |
| 2011/0166636 A1 | 7/2011 | Rowe |
| 2011/0178597 A9 | 7/2011 | Navia et al. |
| 2011/0218619 A1 | 9/2011 | Benichou et al. |
| 2011/0224607 A1 | 9/2011 | Vogelbaum et al. |
| 2011/0300625 A1 | 12/2011 | Paniagua et al. |
| 2011/0301700 A1 | 12/2011 | Fish et al. |
| 2012/0078343 A1 | 3/2012 | Fish |
| 2012/0078356 A1 | 3/2012 | Fish et al. |
| 2012/0095551 A1 | 4/2012 | Navia et al. |
| 2012/0158128 A1 | 6/2012 | Gautam et al. |
| 2012/0185038 A1 | 7/2012 | Fish et al. |
| 2012/0310041 A1 | 12/2012 | Paniagua et al. |

FOREIGN PATENT DOCUMENTS

| | | |
|---|---|---|
| EP | 1441672 | 9/2011 |
| EP | 2055266 | 2/2012 |
| EP | 1621162 | 5/2012 |
| EP | 2260796 | 2/2013 |
| RU | 2355361 C | 5/2009 |
| WO | 91/17720 | 11/1991 |
| WO | 92/17118 | 10/1992 |
| WO | 98/29057 | 7/1998 |
| WO | 99/30646 | 6/1999 |

(56) References Cited

FOREIGN PATENT DOCUMENTS

| | | |
|---|---|---|
| WO | 00/12164 | 3/2000 |
| WO | 01/02031 | 1/2001 |
| WO | 03/47468 | 6/2003 |
| WO | 03/092554 | 11/2003 |
| WO | 2004/026124 | 4/2004 |
| WO | 2006/095342 | 9/2006 |
| WO | 2007/138572 | 12/2007 |
| WO | 2008/082527 | 7/2008 |
| WO | 2008/063537 | 8/2008 |
| WO | 2008/106531 | 9/2008 |
| WO | 2009/052188 | 4/2009 |
| WO | 2009/156471 | 12/2009 |
| WO | 2010/024801 | 3/2010 |
| WO | 2010/027363 | 3/2010 |
| WO | 2010/080594 | 7/2010 |
| WO | 2010/117541 | 10/2010 |
| WO | 2011/109433 | 3/2011 |
| WO | 2011/109450 | 9/2011 |
| WO | 2012/006124 | 1/2012 |
| WO | 2012/040643 | 3/2012 |
| WO | 2012/082952 | 6/2012 |

OTHER PUBLICATIONS

Pavenik, Susan, M.D., PhD et al., "Development and Initial Experimental Evaluation of a Prosthetic Aortic Valve for Transcatherter Placement" Cardivascular Radiology, Apr. 1992, pp. 151-154.

Pick, Adam, "True or False: An Edwards Lifesciences' Tissue Valve Replacement Requires 1,800 Hand-Sewn Stitches" http://heart-valve-surgery.com/heart-surgery-blog/2008/02/26. printed Aug. 13, 2010.

Pohl, M. et al., "In vitro testing of artificial heart valves; comparison between Newtonian and non-Newtonian fluids" Artif Argns, Jan. 1996; 20(1); pp. 37-46.

Purinya, B. et al., "Biomechanical and Structural Properties of the Explanted Bioprosthetic Valve Leaflets" J. of Biomechanis, vol. 27, Iss 1, Jan. 1994 pp. 1-11 Elsevier Science Ltd, 1993.

Sacks, M S et al., "Collagen fiber architecture of bovine pericardium" ASAIO J, Jul. 1, 1994, 40(3):M632-7.

Sacks, M S et al., "A small angle light scattering device for planar connective tissue miscrostructural analysis" Ann Biomed Eng, Jul. 1, 1997, 254(4); 678-89.

Sacks, Michael S, "Incorporation of experimentally-derived fiber orientation into a structural constitutive model for planar collagenous tissues" J. Biomech Eng, Apr. 1, 2003, 125(2); 280-7.

Sacks, Michael S. et al., "Quantification of the fiber architecture and biaxial mechanical behavior of porcine intestinal submucosa" J of Biomedical Research, vol. 46, Iss 1, Jul. 1999, pp. 1-10.

Samouillan, V. et al., "Comparison of chemical treatments on the chain dynamics and thermal stability of bovine pericardium collagen" J Biomed Mater Res A. Feb. 1, 2003;64(2):330-8.

Schoen, Frederick J., "Tissue heart valves: Current challenges and future research perspectives" J of Biomedical Materials Research, vol. 47, Iss 4, Dec. 15, 1999, pp. 439-465.

Sellaro, Tiffany L., "Effects of Collagen Orientation on the Medium-Term Fatigue Response of Heart Valve Biomaterials" 2003, (published thesis) pp. 40-45.

Sellaro, Tiffany L. et al., "Effects of Collagen Fiber Orientation on the Response of Biologically Derived Soft Tissue Biomaterials to Cyclic Loading" J. Biomed Mater Res A 2007, Jan. 2001; 80(1): 194-205); published online Oct. 13, 2006 by Wiley InterScience.

Shandas, Robin PhD et al., "A Method for Determining the Reference Effective Flow Areas for Mechanical Heart Valve Prostheses" Circulation Apr. 25, 2000.

Shen, Ming et al., "Effect of ethanol and ether in the prevention of calcification of bioprostheses" Ann Thorac Surg. May 2001;71(5 Suppl):S413-6.

Shen, Ming et al., "Protein adsorption in glutaraldehyde-preserved bovine pericardium and porcine valve tissues." The Annals of Thoracic Surgery, 2001; 71:409-409.

Simionescu, D et al., "Mapping of glutaraldehyde-treated bovine pericardium and tissue selection for bioprosthetic heart valve" J. Biomed Mater Res, 1993, Jun. 2001:27(6):697-704.

Sun, Wei et al., "Response of heterograft heart valve biomaterials to moderate cyclic loading" J Biomed Mater Res A, Jun. 2004, 69(4); 658-69.

Topol, Eric J., "Textbook of Interventional Cardiology", 1990, Chs. 43-44, pp. 831-867.

Vyavahare, Narendra et al., "Mechanisms of bioprosthetic heart valve failure: Fatigue causes collagen denaturation and glycosaminoglysan loss" J of Biomedical Research, vol. 446, Iss 1, Jul. 1999, pp. 44-50.

Vyavahare, NR et al., "Prevention of Glutaraldehyde-Fixed Bioprosthetic Heart Valve Calcification by Alcohol Pretreatment: Further Mechanistic Studies." J Heart Valve Dis. Jul. 2000;9(4):561-6.

Wiegner, A W et al., "Mechanical and structural correlates of canine pericardium" Circ Res, Sep. 1, 1981m 49(3); 807-14.

Yasui, Takeshi et al., "Determination of collagen fiber orientation in human tissue by use of polarization measurement of molecular second-harmonic-generation light", Applied Optics, vol. 42, No. 14, May 10, 2004, pp. 2861-2867.

Zioupos, P. et al., "Anisotropic Elasticity and Strength of Glutaraldehyde Fixed Bovine Pericardium for Use in Pericardial Bioprosthetic Valves" J. Biomed Mater Res., Jan. 28, 1994(1):49-57.

Zioupos, P. et al., "Mechanical and Optical anisotrophy of bovine pericardium" Med Biol Eng Comput, Jan. 1992; 30(1); pp. 76-82.

Office Action issued in U.S. Appl. No. 10/887,688, dated Nov. 28, 2007 (54813-10100).

Final Office Action issued in U.S. Appl. No. 10/887,688, dated Jul. 15, 2008 (54813-10100).

Office Action issued in U.S. Appl. No. 10/887,688, dated Mar. 16, 2009 (54813-10100).

Examiner Interview Summary issued in U.S. Appl. No. 10/887,688, dated Jun. 12, 2009 (54813-10100).

Final Office Action issued in U.S. Appl. No. 10/887,688, dated Mar. 2, 2010. (54813-10100).

Supplemental Declaration Under 37 CFR 1.131 by inventors filed in U.S. Appl. No. 10/887,688, filed Sep. 14, 2009 (54813-10100).

Supplemental Declaration Under 37 CFR 1.131 by inventors filed in U.S. Appl. No. 10/887,688, filed Feb. 28, 2008 (54813-10100).

Supplemental Declaration Under 37 CFR 1.131 by inventors filed in U.S. Appl. No. 10/887,688, filed Dec. 15, 2008 (54813-10100).

Examiner Interview Summary issued in U.S. Appl. No. 10/887,688, dated Jul. 26, 2010.

Office Action issued in U.S. Appl. No. 10/887,688, dated Feb. 16, 2012 (54813-10100).

Office Action issued Sep. 29, 2010, issued in U.S. Appl. No. 12/228,192 (54813-10110).

Examiner Interview Summary, dated Apr. 5, 2011 in U.S. Appl. No. 12/228,192 (54813-10110).

Final Office Action issued Jul. 14, 2011, in U.S. Appl. No. 12/228,192 (54813-10110).

Office Action issued in U.S. Appl. No. 10/037,266, dated May 8, 2003.

Final Office Action issued in U.S. Appl. No. 10/037,266, dated Mar. 9, 2004.

Affidavit of Dr. Paolo Angelini, M.D., signed Aug. 25, 2009.

Affidavit of Dr. Gervasio A. Lamas, M.D., signed Sep. 3, 2009.

Andersen, H.R. et al., "Transluminal implantation of artificial heart valve" European Heart Journal, 1992, 13, pp. 704-708.

"Artificial heart valve" http://en.wikipedia.org/Artificial_heart_valve, printed May 13, 2009.

Bonhoeffer, Philipp M.D. et al., "Percutaneous Insertion of the Pulmonary Valve" J of the Amer College of Cardiology, vol. 39, No. 10, Elsevier Science, Inc. 2002, pp. 1664-1669, London, UK, and Paris, FR.

Bonhoeffer, Philipp et al., "Percutaeous replacement of pulmonary valve in a right-centricle to pulmonary-artery prosthetic conduit with valve dysfunction" Early Report, The Lacet, vol. 356, Oct. 21, 2000, p. 1403-1405.

Bonhoeffer, Philipp et al., "Transcatherter Implantation of a Bovine Valve in Pulmonary Position: A Lamb Study" Circulation J. of the Amer Heart Assoc, 2000; 102; 813-816.

(56) References Cited

OTHER PUBLICATIONS

Boudjemline, Younes et al., "Percutaneous pulmonary valve replacement in a large right ventricular outflow tract: An experimental study" J. Am. Coll. Cardiol. 2004; 43; 1082-1087.
Braga-Vilela, A. et al., "Extracellular Matrix of Porcine Pericardium; Biochemistry and Collagen Architecture" J. Membr Biol., 2008.
Breuer, Christopher K. M.D. et al., "Application of Tissue-Engineering Principles toward the Development of a Semilunar Heart Valve Substitute" Tissue Engineering, vol. 10, No. 11/12, 2004 pp. 1725-1736.
Cale, A.R. et al., "Revisited: a descending thorasic aortic valve to treat prosthetic valve insufficiency" Ann Thorac Surg, May 1993, 55(5), pp. 1218-2.
Cerrolaza, M et al., "A comparison of the hydrodynamical behaviour of three heart aortic prostheses by numerical methods".
Chew, G.G. et al., Abstract for "Simulation of Damage in a Porcine Prosthetic Heart Valve" J. Med. Eng. Technol., Sep.-Oct. 1999; 23(5): 178-89.
Christie G.W. et al., Abstract for "On Stress Reduction in Bioprosthetic Heart Valve Leaflets by the Use of a Flexible Stent" J. Card Surg, Dec. 1991; 6(4) pp. 476-481.
"Collagen" http://en.wikipedia.org/wiki/Collagen, printed May 13, 2009.
Collins, J. J., Jr, "The Evolution of artificial heart valve" N. Engl J Med, Feb. 28, 1991; 324(9):624-6.
Corden, J. et al., "The influence of open leaflet geometry on the haemodynamic flow characteristics of polyrethane trileaflet artificial heart valve" PubMed medline query, p. 1 of 1.
Cribier, Alain et al., "Percutaneious Transcatheter Implantation of an Aoritc Valve Prosthesis for Calcific Aortic Stenosis: First Human Case Description" Circulation J of the Amer Heart Assoc, originally published online Nov. 25, 2002.
Edwards Lifesciences Receives FDA Approval for New Heart Valve, http:www.medicalnewstoday.com/articles/149588.php, May 11, 2009.
Fish, R. David, "Percutaneous Heart Valve Replacement: Enthusiasm Tempered" Circulation J of the Amer Heart Assoc, 2004; 110; 1876-1878.
Fishbein, M.C. et al., "Cardiac pathology after aortic valve replacement using Hufnagel trileaflet prostheses: study of 20 necropsy patients" Ann Heart J., Apr. 1975, 89(4), pp. 443-448.
Gloeckner, D. Claire et al., "Mechanical Evaluation and Design of a Multilayered Collagenous Repair Biomaterial" J. of Biomedical Materials Research Part A, vol. 52 Iss 2, pp. 365-373, Published online Aug. 15, 2000, Wiley Periodicals, Inc.
Grube E., et al., Abstract for "Progress and Current Status of Percutaneous Aortic Valve Replacement: Results of Three Device Generations of the CoreValve Revalving System", Circ. Cardiovasc Intervent. 2008;1:167-175.
Hanlon, JG et al., "Pre-use intraoperative testing of autologous tissue for valvular surgery: a proof of concept study" J. Heart Valve Dis, Nov. 1999; 8(6); pp. 614-623.
Bech-Hanssen, Odd, M.D. et al., "Aortic Prosthetic Valve Desing and Size: Relation to Doppler Echocardiographic Finding and Pressure Recovery—An In Vitro Study" J. Am Soc Echocardiography 2000; 13:39-50.
Hasenkam, J.M. et al., "A model for acute haemodynamic studies in the ascending aorta in pigs" Cardiovasc Res, Jul. 1988, 22(7), pp. 464-471.
Hiester,E.D. et al., "Optimal bovine pericardial tissue selection sites. I. Fiber architecture and tissue thickness measurements." J. Biomed Mater Res, 1998, Feb. 2001; 39(2):207-14.
Hufnagel, Charles A., M.D., "Basic Concepts in the Development of Cardiovascular Prosthes" The American Journal of Surgery, vol. 137, Mar. 1979.
Hufnagel, Charles.A., MD et al., "In the beginning. Surgical Correction of Aortic Insufficiency" 1954; Ann Thorac Surg May 1989; 47(3), pp. 475-476.
Hufnagel, Charles.A., MD et al., "Late follow-up of ball-valve prostheses in the descending thoracic aortia", J. Throrac Cardiovasc Surg, Dec. 1976, 72(6), pp. 900-909.
Hufnagel, Charles.A., MD et al., "Surgical Correction of Aortic Insufficiency" Surgery vol. 35, May 1954 No. 5.
Hufnagel, Charles A., "Vessels and Valves", Sec. 1: Development of Cardiac Surgery, Chap 7, pp. 43-55.
Introduction to Stereomicroscopy, http://www.microscopyu.com/articles/stereomicroscopy/stereointro.html, Copyright 2000-2012, printed on Mar. 15, 2012.
Iopatch(R) Tutoplast(R) Processed Pericardium Directions for Use; http://www.iopinc.com/surgeons_and_medical_professionals/iopatch/directions.asp, printed on Jun. 2, 2009.
Knudsen, LL et al., "Catheter-implanted prosthetic heart valves. Transluminal catheter implantation of a new expandable artificial heart valve in the descending thoracic aorta in isolated vessels and closed chest pigs" Int J. Artif Organs, May 1993, 16(5); pp. 253-262.
Lax, Jorge A., M.D., et al. "Estimation of the Ejection Fraction in Patients with Myocardial Infarction Obtained from the Combined Index of Systolic and Diastolic Left Ventricular Function: A New Method" J of the American Soc of Echocardiography, vol. 13, No. 2.
Liao, Jun et al., "Molecular orientation of collagen in intact planar connective tissues under biaxial stretch" Acta Biomateriala, vol. 1, Iss. 1, Jan. 2005, pp. 45-54.
Liao, K X et al., "Two-dimensional mechanical and ultrastructural correlates of bovine pericardium for prosthetic valves" ASAIO Trans, Jun. 1, 1991, 37(3); M341-51.
LS, Yu et al., "New Polyurethane valves in new soft artificial heart" ASAIO Trans Jul.-Sep. 1989; 35(3), pp. 301-304.
Mirnajafi, A. et al. "The effects of collagen fiber orientation of the flexural properties of pericardial heterograft biomaterials" Biomaterials, Mar. 2005; 26(7): 795-804.
Mirzaie, M. et al., "A new storage solution for porcine aortic valves" Ann Thorac Cardiovasc Surg. Apr. 2007;13(2):102-9.
Moazami, N. et al., "Transluminal aortic valve placement. A feasibility study with a newly designed collapsible aortic valve" ASAIO J, Sep.-Oct. 1996, 42(5):M 381-5.
Nienaber C., M.D. et al., "Nonsurgical Reconstruction of Thoracic Aortic Dissection by Stent-Graft Placement" N. Eng. J. Med, May 20, 1999, col. 340, No. 20.
Noorlander, Maril L. et al., "A Quantitative Method to Determine the Orientation of Collagen Fibers in the Dermis" The J. of Histochemistry & Cytochemistry, vol. 50(11): 2002, pp. 1469-1474.
Nunn, D.B., "Structural Failure of Dacron Arterial Grafts" Seminars in Vascular Surgery, col. 12, No. 1 Mar. 1999, pp. 88-91.
Optical Microscope, Wikipedia, http://en.wikipedia.org/wiki/Stereomiscroscope, May 13, 2009.
Orthogonality, http://en.wikipedia.org/wiki/Orthogonal, May 13, 2009.
Paniagua, David, et al., Percutaneous Heart Valve in the Chronic In Vitro Testing Model, Circulation, 2002, pp. 51-52, vol. 106, American Heart Association, US.
Paniagua, David et al., First Human Case of Retrograde Transcatheter Implantation of an Aortic Valve Prosthesis, Texas Heart Institute Journal, 2005, pp. 91-96, vol. 32, US.
Paniagua, David et al., Abstract 4622: "Percutaneous Implantation of a Low Profile, Dry Membrane, Heart Valve in an Integrated Delivery System in the Aortic and Pulmonary Positions: One-month Animal Results," Circulation, American Heart Association, Inc., 2009; 120: S982.

* cited by examiner

PERCUTANEOUSLY IMPLANTABLE REPLACEMENT HEART VALVE DEVICE AND METHOD OF MAKING SAME

CONTINUITY INFORMATION

The present application is a continuation application of U.S. patent application Ser. No. 13/675,665 filed on Nov. 13, 2012, which is a continuation application of U.S. patent application Ser. No. 10/887,688 filed on Jul. 10, 2004, now U.S. Pat. No. 8,308,797, which is a continuation-in-part application of U.S. patent application Ser. No. 10/037,266, filed on Jan. 4, 2002 (now abandoned). All of the foregoing applications are incorporated herein by reference in their entireties.

BACKGROUND OF THE INVENTION

1. Field of the Invention

The present invention is in the field of heart valve replacement. More specifically, the present invention is directed to a method of making a percutaneously implantable replacement heart valve.

2. Description of Related Art

There have been numerous efforts in the field of heart valve replacement to improve both the durability and effectiveness of replacement heart valves as well as the ease of implantation. A brief description of heart valves and heart function follows to provide relevant background for the present invention.

There are four valves in the heart that serve to direct the flow of blood through the two sides of the heart in a forward direction. On the left (systemic) side of the heart are: 1) the mitral valve, located between the left atrium and the left ventricle, and 2) the aortic valve, located between the left ventricle and the aorta. These two valves direct oxygenated blood coming from the lungs through the left side of the heart into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct de-oxygenated blood coming from the body through the right side of the heart into the pulmonary artery for distribution to the lungs, where it again becomes re-oxygenated to begin the circuit anew.

Heart valves are passive structures that simply open and close in response to differential pressures on either side of the particular valve. They consist of moveable "leaflets" that are designed simply to open and close in response to differential pressures on either side of the valve's leaflets. The mitral valve has two leaflets and the tricuspid valve has three. The aortic and pulmonary valves are referred to as "semilunar valves" because of the unique appearance of their leaflets, which are more aptly termed "cusps" and are shaped somewhat like a half-moon. The aortic and pulmonary valves each have three cusps.

In general, the components of heart valves include the valve annulus, which will remain as a roughly circular open ring after the leaflets of a diseased or damaged valve have been removed; leaflets or cusps; papillary muscles which are attached at their bases to the interior surface of the left or right ventricular wall; and multiple chordae tendineae, which couple the valve leaflets or cusps to the papillary muscles. There is no one-to-one chordal connection between the leaflets and the papillary muscles; instead, numerous chordae are present, and chordae from each papillary muscle attach to both of the valve leaflets.

When the left ventricular wall relaxes so that the ventricular chamber enlarges and draws in blood, the leaflets of the mitral valve separate and the valve opens. Oxygenated blood flows in a downward direction through the valve, to fill the expanding ventricular cavity. Once the left ventricular cavity has filled, the left ventricle contracts, causing a rapid rise in the left ventricular cavitary pressure. This causes the mitral valve to close while the aortic valve opens, allowing the oxygenated blood to be ejected from the left ventricle into the aorta. The chordae tendineae of the mitral valve prevent the mitral leaflets from prolapsing back into the left atrium when the left ventricular chamber contracts.

The three leaflets, chordae tendineae, and papillary muscles of the tricuspid valve function in a similar manner, in response to the filling of the right ventricle and its subsequent contraction. The cusps of the aortic valve also respond passively to pressure differentials between the left ventricle and the aorta. When the left ventricle contracts, the aortic valve cusps open to allow the flow of oxygenated blood from the left ventricle into the aorta. When the left ventricle relaxes, the aortic valve cusps reapproximate to prevent the blood which has entered the aorta from leaking (regurgitating) back into the left ventricle. The pulmonary valve cusps respond passively in the same manner in response to relaxation and contraction of the right ventricle in moving de-oxygenated blood into the pulmonary artery and thence to the lungs for re-oxygenation. Neither of these semilunar valves has associated chordae tendineae or papillary muscles.

Problems that can develop with heart valves consist of stenosis, in which a valve does not open properly, and/or insufficiency, also called regurgitation, in which a valve does not close properly. In addition to stenosis and insufficiency of heart valves, heart valves may need to be surgically repaired or replaced due to certain types of bacterial or fungal infections in which the valve may continue to function normally, but nevertheless harbors an overgrowth of bacteria (vegetation) on the leaflets of the valve that may embolize and lodge downstream in a vital artery. If such vegetations are on the valves of the left side (i.e., the systemic circulation side) of the heart, embolization may occur, resulting in sudden loss of the blood supply to the affected body organ and immediate malfunction of that organ. The organ most commonly affected by such embolization is the brain, in which case the patient suffers a stroke. Thus, surgical replacement of either the mitral or aortic valve (left-sided heart valves) may be necessary for this problem even though neither stenosis nor insufficiency of either valve is present. Likewise, bacterial or fungal vegetations on the tricuspid valve may embolize to the lungs resulting in a lung abscess and therefore, may require replacement of the tricuspid valve even though no tricuspid valve stenosis or insufficiency is present.

These problems are treated by surgical repair of valves, although often the valves are too diseased to repair and must be replaced. If a heart valve must be replaced, there are currently several options available, and the choice of a particular type of artificial valve depends on factors such as the location of the valve, the age and other specifics of the patient, and the surgeon's experiences and preferences. Currently in the United States over 100,000 defective heart valves are replaced annually, at an approximate cost of $30-50,000 per procedure, and thus it would be desirable if heart valves could be replaced using minimally invasive techniques and without having to repeat the procedure within a matter of years due to the lack of durability of the replacement heart valve. It would be especially advantageous if a defective heart valve could be removed via an endovascular procedure, that is, a procedure where the invasion into the body is through a blood vessel such as the femoral artery. The procedure is then carried out percutaneously and transluminally using the vascular system to convey appropriate devices to the position in the body wherein it is desired to carry out the desired procedure. An example of such a procedure would be angioplasty, wherein a catheter carrying a small balloon at its distal end is manipulated through the body's vessels to a point where there is a blockage in a vessel. The balloon is expanded to create an opening in the blockage, and then the balloon is deflated and the catheter and balloon are removed from the vessel.

Endovascular procedures have substantial benefits both from the standpoint of health and safety as well as cost. Such procedures require minimal invasion of the human body, and there is consequently considerable reduction and in some instances even elimination, of the use of a general anesthesia and much shorter hospital stays.

Replacement heart valves can be categorized as either artificial mechanical valves, transplanted valves and tissue valves. Replacement heart valves are designed to optimize hemodynamic performance, thrombogenicity and durability. Another factor taken into consideration is the relative ease of surgical implantation.

Mechanical valves are typically constructed from nonbiological materials such as plastics, metals and other artificial materials which, while durable, are expensive and prone to blood clotting which increases the risk of an embolism. Anticoagulants taken to help against blood clotting can further complicate the patient's health due to increased risks for hemorrhages.

Transplanted valves are natural valves taken from cadavers. These valves are typically removed and frozen in liquid nitrogen, and are stored for later use. They are typically fixed in glutaraldehyde to eliminate antigenicity and are sutured in place, typically with a stent.

Artificial tissue valves are valves constructed from animal tissue, such as bovine or porcine tissue. Efforts have also been made at using tissue from the patient for which the valve will be constructed.

Most tissue valves are constructed by sewing the leaflets of pig aortic valves to a stent to hold the leaflets in proper position, or by constructing valve leaflets from the pericardial sac of cows or pigs and sewing them to a stent. The porcine or bovine tissue is chemically treated to alleviate any antigenicity. The pericardium is a membrane that surrounds the heart and isolates it from the rest of the chest wall structures. The pericardium is a thin and very slippery, which makes it difficult for suturing in a millimetricly precise way. The method of making the replacement heart valve of the present invention solves this problem through a process that includes drying and compressing the pericardium using photo-mechanical compression in such a way that makes it possible to handle and fold the material more easily.

For example, one prior replacement heart valve requires each sculpted leaflet to be trimmed in a way that forms an extended flap, which becomes a relatively narrow strand of tissue near its tip. The tip of each pericardial tissue strand is sutured directly to a papillary muscle, causing the strand to mimic a chordae tendineae. Each strand extends from the center of a leaflet in the valve, and each strand is sutured directly to either an anterior and posterior papillary muscle. This requires each leaflet to be positioned directly over a papillary muscle. This effectively rotates the leaflets of the valve about 90 degrees as compared to the leaflets of a native valve. The line of commissure between the leaflets, when they are pressed together during systole, will bisect (at a perpendicular angle) an imaginary line that crosses the peaks of the two papillary muscles, instead of lying roughly along that line as occurs in a native valve.

A different approach to creating artificial tissue valves is described in U.S. Pat. No. 5,163,955 to Calvin, et al. and U.S. Pat. Nos. 5,571,174 and 5,653,749 to Love. Using a cutting die, the pericardial tissue is cut into a carefully defined geometric shape, treated with glutaraldehyde, then clamped in a sandwich-fashion between two stent components. This creates a tri-leaflet valve that resembles an aortic or pulmonary valve, having semilunar-type cusps rather than atrioventricular-type leaflets.

U.S. Pat. No. 3,671,979 to Moulopoulos describes an endovascularly inserted conical shaped umbrella-like valve positioned and held in place by an elongated mounting catheter at a supra-annular site to the aortic valve in a nearby arterial vessel. The conical end points toward the malfunctioning aortic valve and the umbrella's distal ends open up against the aorta wall with reverse blood flow, thereby preventing regurgitation.

U.S. Pat. No. 4,056,854 to Boretos describes an endovascularly inserted, catheter mounted, supra-annular valve in which the circular frame abuts the wall of the artery and attached flaps of flexible membrane extend distally in the vasculature. The flaps lie against the artery wall during forward flow, and close inward towards the central catheter to prevent regurgitation during reverse blood flow. The Boretos valve was designed to be positioned against the artery wall during forward flow, as compared to the mid-center position of the Moulopoulos valve, to reduce the stagnation of blood flow and consequent thrombus and embolic formation expected from a valve at mid-center position.

The main advantage of tissue valves is that they do not cause blood clots to form as readily as do the mechanical valves, and therefore, they do not absolutely require systemic anticoagulation. The major disadvantage of tissue valves is that they lack the long-term durability of mechanical valves. Tissue valves have a significant failure rate, usually within ten years following implantation. One cause of these failures is believed to be the chemical treatment of the animal tissue that prevents it from being antigenic to the patient. In addition, the presence of extensive suturing prevents the artificial tissue valve from being anatomically accurate in comparison to a normal heart valve, even in the aortic valve position.

A shortcoming of prior artificial tissue valves has been the inability to effectively simulate the exact anatomy of a native heart valve. Although transplanted human or porcine aortic valves have the gross appearance of native aortic valves, the fixation process (freezing with liquid nitrogen, and chemical treatment, respectively) alters the histologic characteristics of the valve tissue. Porcine and bovine pericardial valves not only require chemical preparation (usually involving fixation with glutaraldehyde), but the leaflets must be sutured to cloth-covered stents in order to hold the leaflets in position for proper opening and closing of the valve. Additionally, the leaflets of most such tissue valves are constructed by cutting or suturing the tissue material, resulting in leaflets that do not duplicate the form and function of a real valve and are more susceptible to failure.

SUMMARY OF THE INVENTION

The present invention is a replacement heart valve device and method of making same. The replacement heart valve device, in a preferred embodiment, comprises a stent made of stainless steel or self-expanding nitinol and a completely newly designed artificial biological tissue valve disposed within the inner space of the stent. The cusp or leaflet portion of the valve means is formed by folding of the pericardium material preferably used to create the valve without cutting of slits to form leaflets or suturing or otherwise affixing of separate leaflet portions. Other forms of tissue and suitable synthetic materials can also be used for the valve, formed in a sheet of starting material. The folded design provides a number of advantages over prior designs, including improved resistance to tearing at suture lines. The cusps/leaflets open in response to blood flow in one direction and close in response to blood flow in the opposite direction. Preferably the tubular portion of the valve means contains the same number of cusps as the native valve being replaced, in substantially the same size and configuration. The outer surface of the valve means is attached to the stent member.

The replacement heart valve device is preferably implanted using a delivery system having a central part which consists of a flexible hollow tube catheter that allows a metallic guide wire to be advanced inside it. The stented valve is collapsed over the central tube and it is covered by a movable sheath. The sheath keeps the stented valve in the collapsed position. Once the cover sheath is moved backwards, the stented valve can be deployed. The endovascular stented-valve, in a preferred embodiment, is a glutaraldehyde fixed mammal pericardium or synthetic biocompatible material which has two or three cusps that open distally to permit unidirectional blood flow. The stent can either be self-expanding or the stent can be expandable through use of a balloon catheter.

The present invention also comprises a method of making a replacement heart valve device. In order to make the valve, the pericardium starting material is isolated and all the fat tissue and extra fibers are removed. The biological membrane material is cleaned by mechanical separation of unwanted layers using hydromechanical force means. Once the pericardium is completely clean, the material is dried in order to make it easier to handle and fold. Preferably, this drying is done by exposing the biocompatible membrane material to photomechanical compression to remove all lipids from the pericardium or other biocompatible membrane material and to cause protein denaturalization, transforming the material into a stronger and more homogeneous surface. The valve is formed by taking a flat sheet of the material and folding in such a way that forms a three-leaflet or other number of leaflet valve. Then it is placed in a sequence of solutions, one of isopropyl alcohol of about 70-100%, one of ethanol of about 70-100%, one of glycerol and one of glutaraldehyde, preferably at a concentration of about 0.07-25% for approximately 36 hours. The material is dried in order to make it easier to handle and fold. Preferably this drying is done by exposing the biocompatible membrane material to light and then mechanically compressing the material to cause protein denaturation. This results in material that is stronger and more homogeneous. The valve is formed by taking a flat sheet of bovine or porcine pericardium and folding it in such a way that forms a three-leaflet valve. The valve can also be made in the same manner from fresh, cryopreserved or glutaraldehyde fixed allografts or xenografts or synthetic non-biological, non-thrombogenic material. The folding of the pericardium material to create the cusps or leaflets reduces the extent of suturing otherwise required, and resembles the natural form and function of the valve leaflets. The cleaning, pressing and drying technique used to create the valve material makes the folding more practicable. The valve is rehydrated after being formed. The method of the present invention also greatly reduces the risk of tearing of the cusps or leaflets, since they are formed by folding a single uncut portion of material forming the valve rather than being attached by suturing.

Once the endovascular implantation of the prosthetic valve device is completed in the host, the function of the prosthetic valve device can be monitored by the same methods as used to monitor valve replacements done by open heart surgery. Routine physical examination, periodic echocardiography or angiography can be performed. In contrast to open heart surgery, however, the host requires a short recovery period and can return home within one day of the endovascular procedure. The replacement heart valve device of the present invention can be used in any patient where bioprosthetic valves are indicated, namely elderly patients with cardiac valve diseases, and patients unable to tolerate open heart procedures or life-long anticoagulation medication and treatment. The present invention can be practiced in applications with respect to each of the heart's valves.

DESCRIPTION OF A PREFERRED EMBODIMENT

Figure 1:
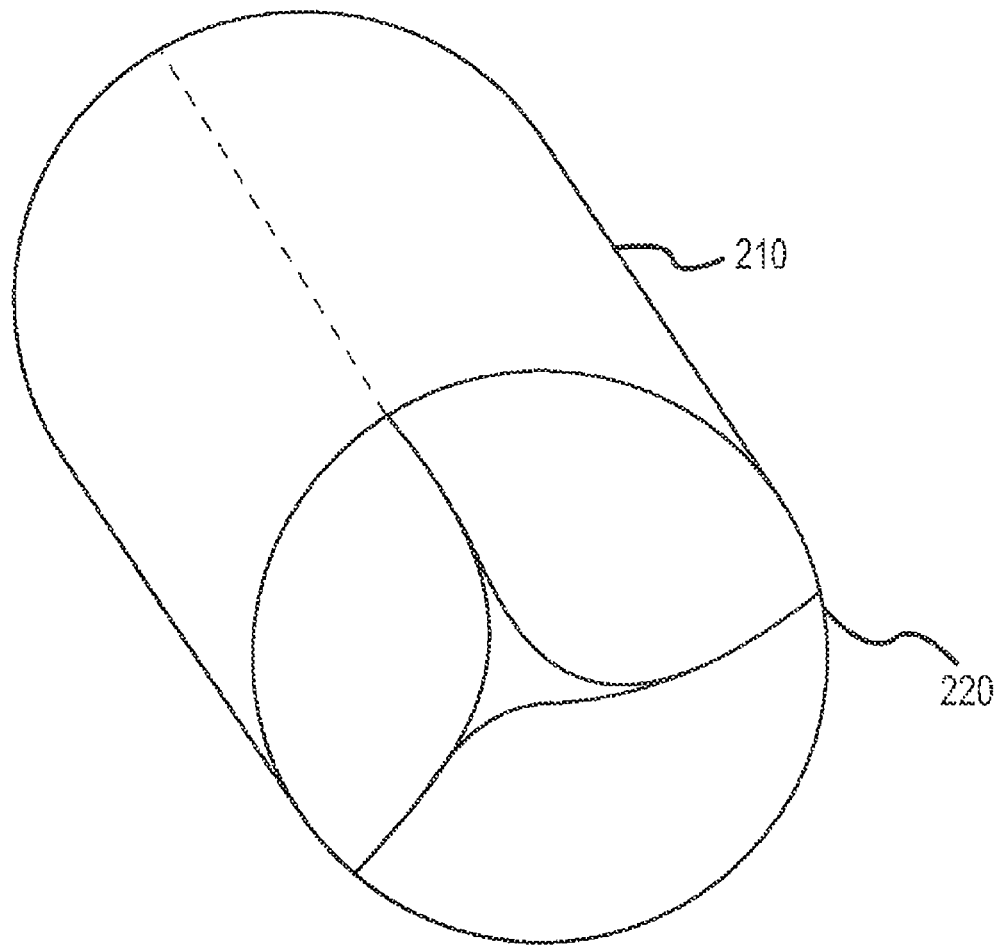
FIG. 1 depicts a side perspective view of the replacement heart valve device of the present invention in one embodiment with the valve in the closed position.
Figure 2:
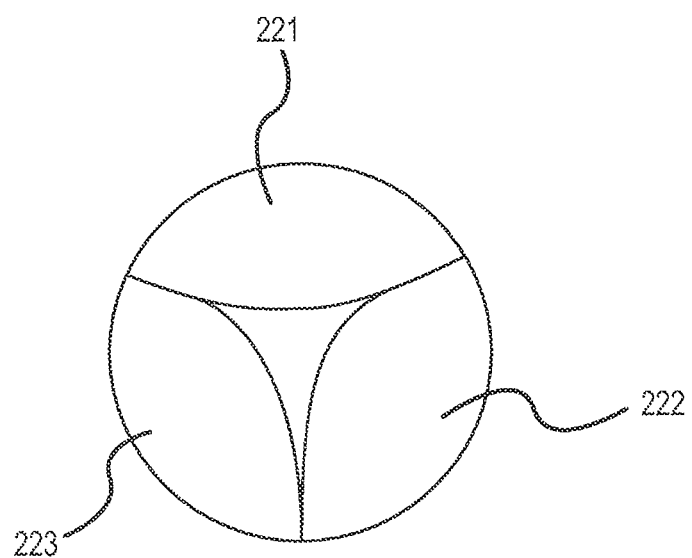
FIG. 2 depicts the folds which form the leaflets or cusps of the replacement heart valve of the present invention in one embodiment.
Figure 7:
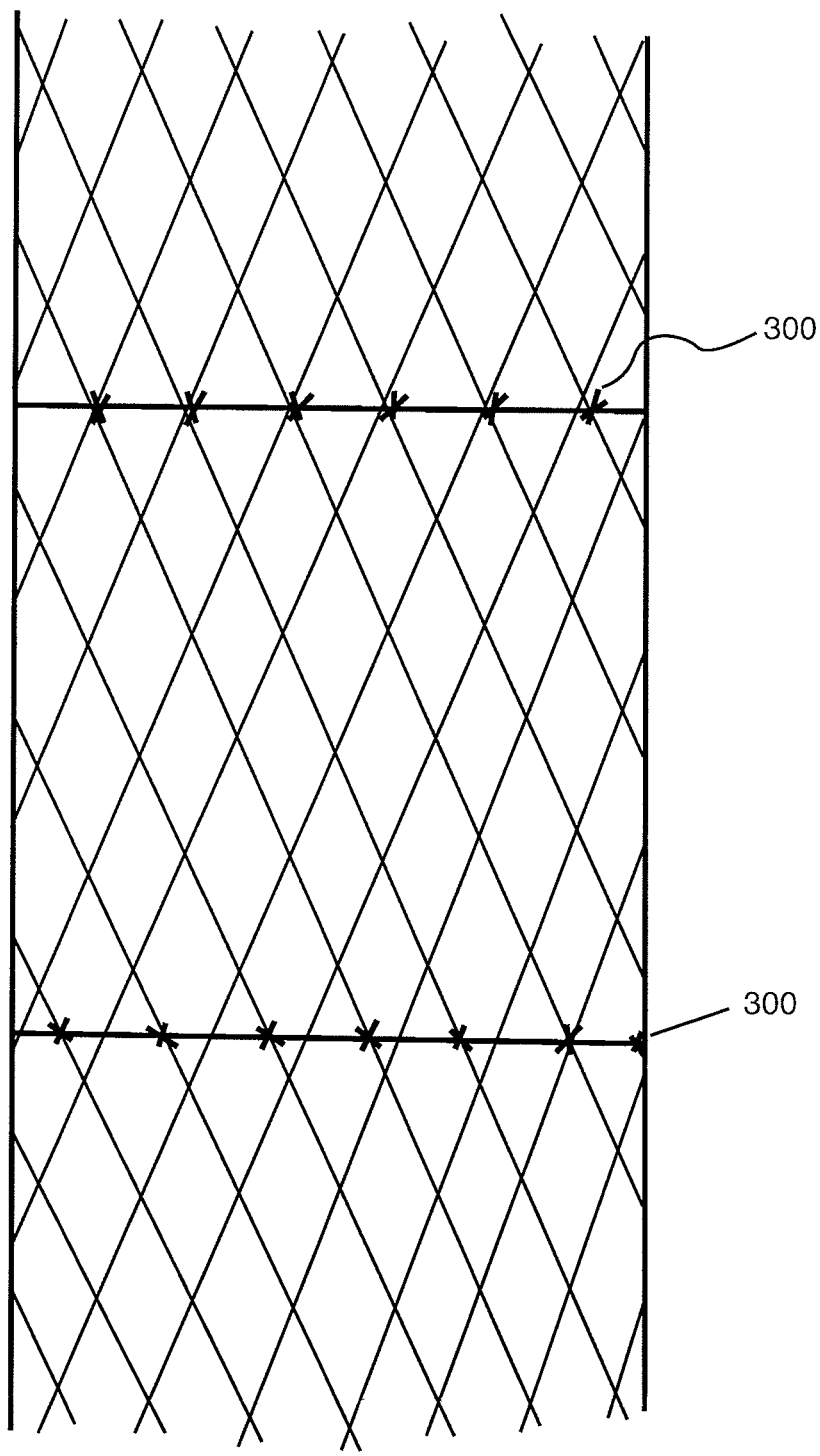
FIG. 7 depicts the suture points of one embodiment of the replacement heart valve device of the present invention.

The present invention comprises a percutaneously implantable replacement heart valve and a method for making same. The artificial heart valve device of the present invention is capable of exhibiting a variable diameter between a compressed or collapsed position and an expanded position. A preferred embodiment of the replacement heart valve device according to the present invention is set forth in FIG. 5. The replacement heart valve device comprises a stent member 100 and a flexible valve means 200. The stent member 100 is preferably self-expanding, although balloon-expandable stents can be used as well, and has a first polygonal shape in its compressed or collapsed configuration and a second, larger polygonal shape in its expanded configuration. Referring to FIG. 1, the valve means 200 comprises a generally tubular portion 210 and, preferably, a peripheral upstanding cusp or leaflet portion 220. The valve means 200 is disposed within the cylindrical stent member 100 with the tubular portion 210 transverse of and at some acute angle relative to the stent walls. The diameter of the tubular portion 210 is substantially the same as the inside diameter of the stent member in its initial expanded configuration. The peripheral upstanding cusp or leaflet portion 220 is disposed on valve means 200 substantially parallel to the walls of the stent member similar to a cuff on a shirt. The cusp or leaflet portion 220 of the valve means 200 is generally tubular in shape and comprises three leaflets 221, 222 and 223 as shown, although it is understood that there could be from two to four leaflets. The tubular portion of the valve means 200 is attached to the stent member 100 by a plurality of sutures 300, as depicted in FIG. 7.

The leaflet portion 220 of the valve means 200 extends across or transverse of the cylindrical stent 100. The leaflets 221, 222 and 223 are the actual valve and allow for one-way flow of blood. The leaflet portion 220 as connected to the rest of the valve resembles the cuff of a shirt. FIG. 9 depicts the folds preferred for valve cusp and leaflet formation involving three leaflets. The configuration of the stent member 100 and the flexible, resilient material of construction allows the valve to collapse into a relatively small cylinder as seen in FIG. 6. The replacement heart valve will not stay in its collapsed configuration without being restrained. Once the restraint is removed, the self-expanding stent member 100 will cause the artificial heart valve to take its expanded configuration, as seen in FIG. 5.

Stent Member

Figure 5:
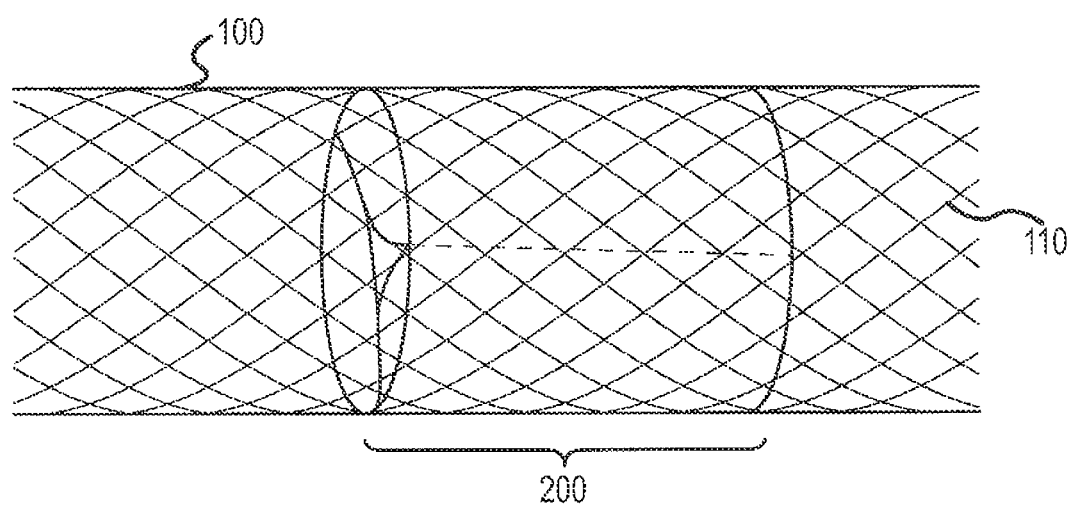
FIG. 5 depicts a side view of one embodiment of the replacement heart valve device of the present invention mounted within a self-expanding stent, with the stent in the expanded position.
Figure 6:
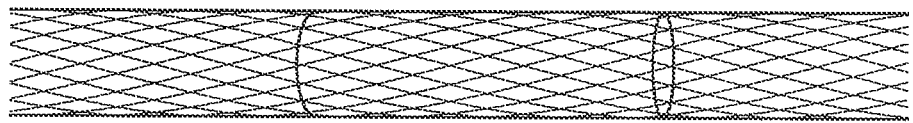
FIG. 6 depicts a side perspective view of one embodiment of the replacement heart valve device of the present invention mounted within a self-expanding stent in the collapsed position.
Figure 8:
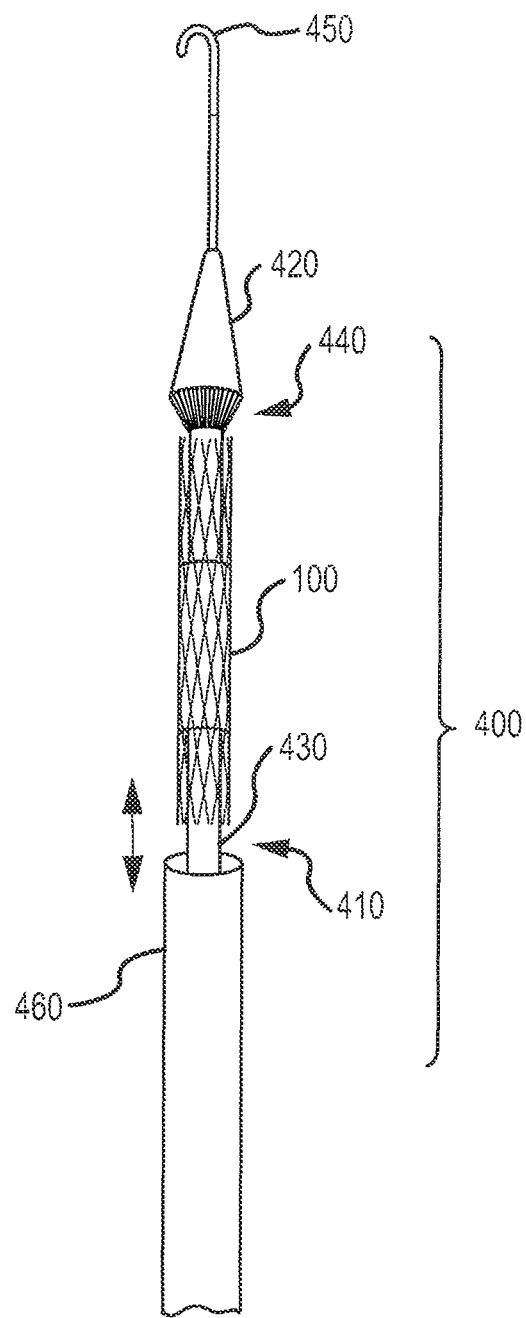
FIG. 8 depicts the implantation/delivery system used with the present invention in a preferred embodiment.

The stent member 100 preferably comprises a self-expanding nickel-titanium alloy stent, also called "nitinol," in a sine wave-like configuration as shown in FIG. 5. An enlarged view of a preferred embodiment of the stent member for use in the replacement heart valve of the invention is depicted in FIG. 5. The stent member 100 includes a length of wire 110 formed in a closed zigzag configuration. The wire can be a single piece, stamped or extruded, or it could be formed by welding the free ends together. The straight sections of the stent member 100 are joined by bends. The stent is readily compressible to a small cylindrical shape as depicted in FIGS. 6 and 8, and resiliently self-expandable to the shape shown in FIG. 5.

The stent member 100 of the artificial heart valve device of the present invention may be made from various metal alloys, titanium, titanium alloy, nitinol, stainless steel, or other resilient, flexible non-toxic, non-thrombogenic, physiologically acceptable and biocompatible materials. The configuration may be the zigzag configuration shown or a sine wave configuration, mesh configuration or a similar configuration which will allow the stent to be readily collapsible and self-expandable. When a zigzag or sine wave configured stent member is used, the diameter of the wire from which the stent is made is preferably from about 0.010 to 0.035 inches and still, preferably from about 0.012 to 0.025 inches. The diameter of the stent member will be from about 1.5 to 3.5 cm, preferably from about 1.75 to 3.00 cm, and the length of the stent member will be from about 1.0 to 10 cm, preferably from about 1.1 to 5 cm.

The stent used in a preferred embodiment of the present invention is fabricated from a "shaped memory" alloy, nitinol, which is composed of nickel and titanium. Nitinol wire is first fashioned into the desired shape for the device and then the device is heat annealed. A meshwork of nitinol wire of approximately 0.008 inch gauge is formed into a tubular structure with a minimum central diameter of 20 mm to make the stent. Away from its central portion, the tubular structure flares markedly at both ends in a trumpet-like configuration. The maximum diameter of the flared ends of the stent is approximately 50 mm. The purpose of the stent is to maintain a semi-rigid patent channel through the diseased cardiac valve following its implantation.

When the components of the replacement heart valve device are exposed to cold temperatures, they become very flexible and supple, allowing them to be compressed down and pass easily through the delivery sheath. A cold temperature is maintained within the sheath during delivery to the deployment site by constantly infusing the sheath with an iced saline solution. Once the valve components are exposed to body temperature at the end of the sheath, they instantaneously reassume their predetermined shapes, thus allowing them to function as designed.

Preferably the stent member 100 carries a plurality of barbs extending outwardly from the outside surface of the stent member for fixing the heart valve device in a desired position. More preferably the barbs are disposed in two spaced-apart, circular configurations with the barbs in one circle extending in an upstream direction and the barbs in the other circle extending in a downstream direction. It is especially preferable that the barbs on the inflow side of the valve point in the direction of flow and the barbs on the outflow side point in the direction opposite to flow. It is preferred that the stent be formed of titanium alloy wire or other flexible, relatively rigid, physiologically acceptable material arranged in a closed zigzag configuration so that the stent member will readily collapse and expand as pressure is applied and released, respectively.

Valve Means

The valve means 200 is flexible, compressible, host-compatible, and non-thrombogenic. The valve means 200 can be made from various materials, for example, fresh, cryopreserved or glutaraldehyde fixed allografts or xenografts. Synthetic biocompatible materials such as polytetrafluoroethylene, polyester, polyurethane, nitinol or other alloy/metal foil sheet material and the like may be used. The preferred material for the valve means 200 is mammal pericardium tissue, particularly juvenile-age animal pericardium tissue. The valve means 200 is disposed within the cylindrical stent member 100 with the tubular portion 210 transverse of and at some acute angle relative to the stent walls. The diameter of the tubular portion 210 is substantially the same as the inside diameter of the stent member 100 in its initial expanded configuration. The peripheral upstanding cusp or leaflet portion 220 is disposed substantially parallel to the walls of the stent member 100 similar to a cuff on a shirt.

Figure 3A:
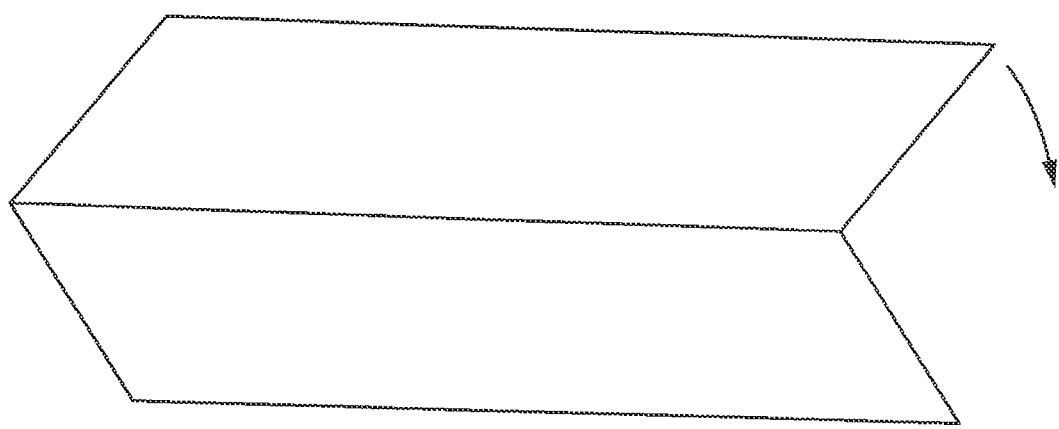
FIGS. 3A and 3B depict a preferred procedure for folding the pericardium tissue starting material to create the replacement heart valve of the present invention.
Figure 3B:
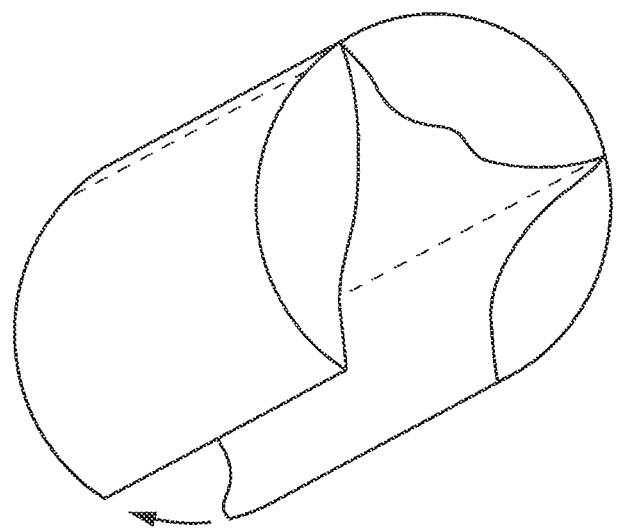
Figure 4:
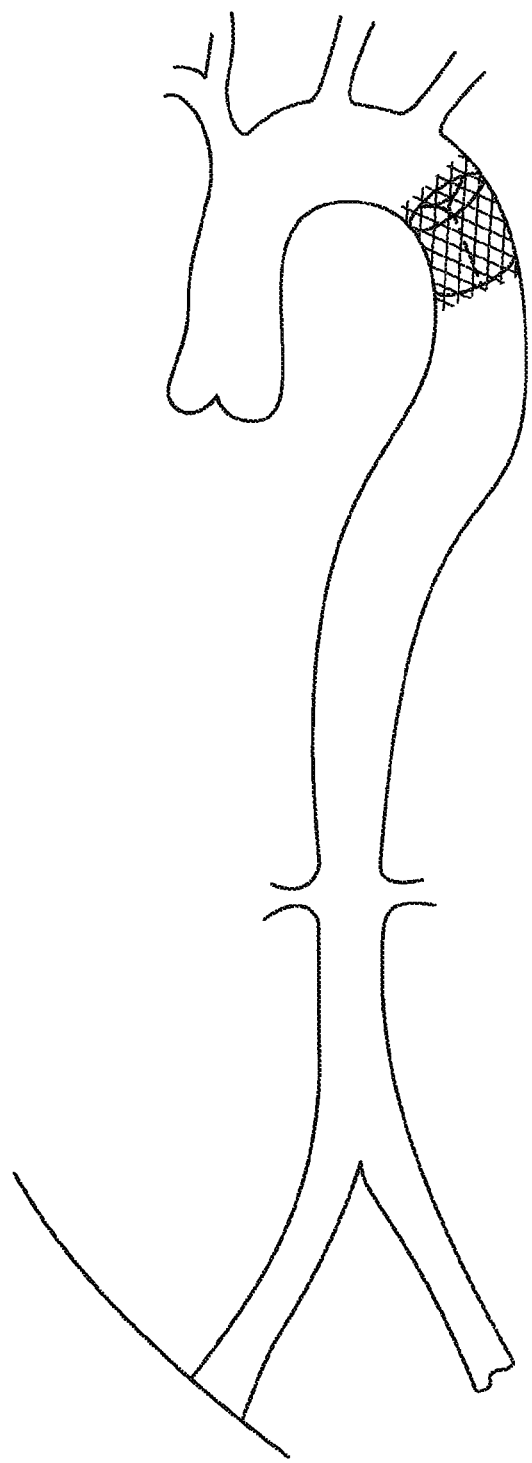
FIG. 4 depicts a side perspective view of the replacement heart valve device of the present invention in one embodiment represented as if implanted within an artery.
Figure 9A:
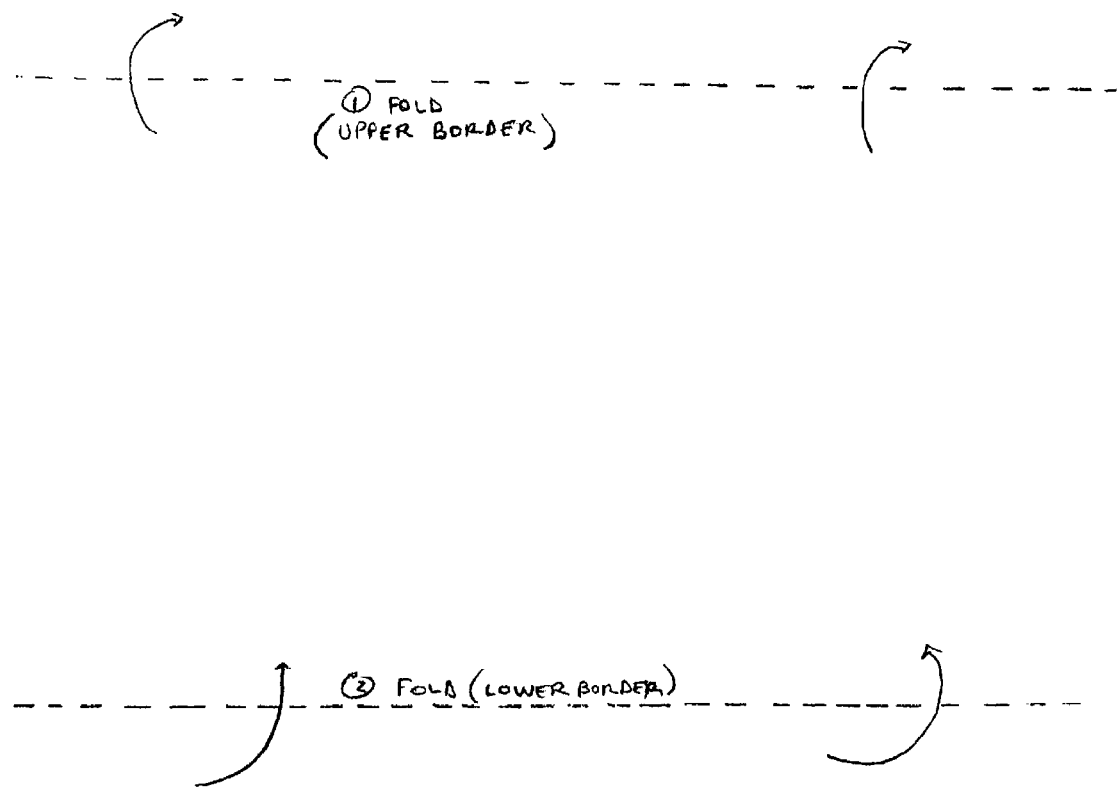
FIGS. 9A, 9B and 9C depict a representation of a sheet of biocompatible valve material showing preferred folds.
Figure 9B:
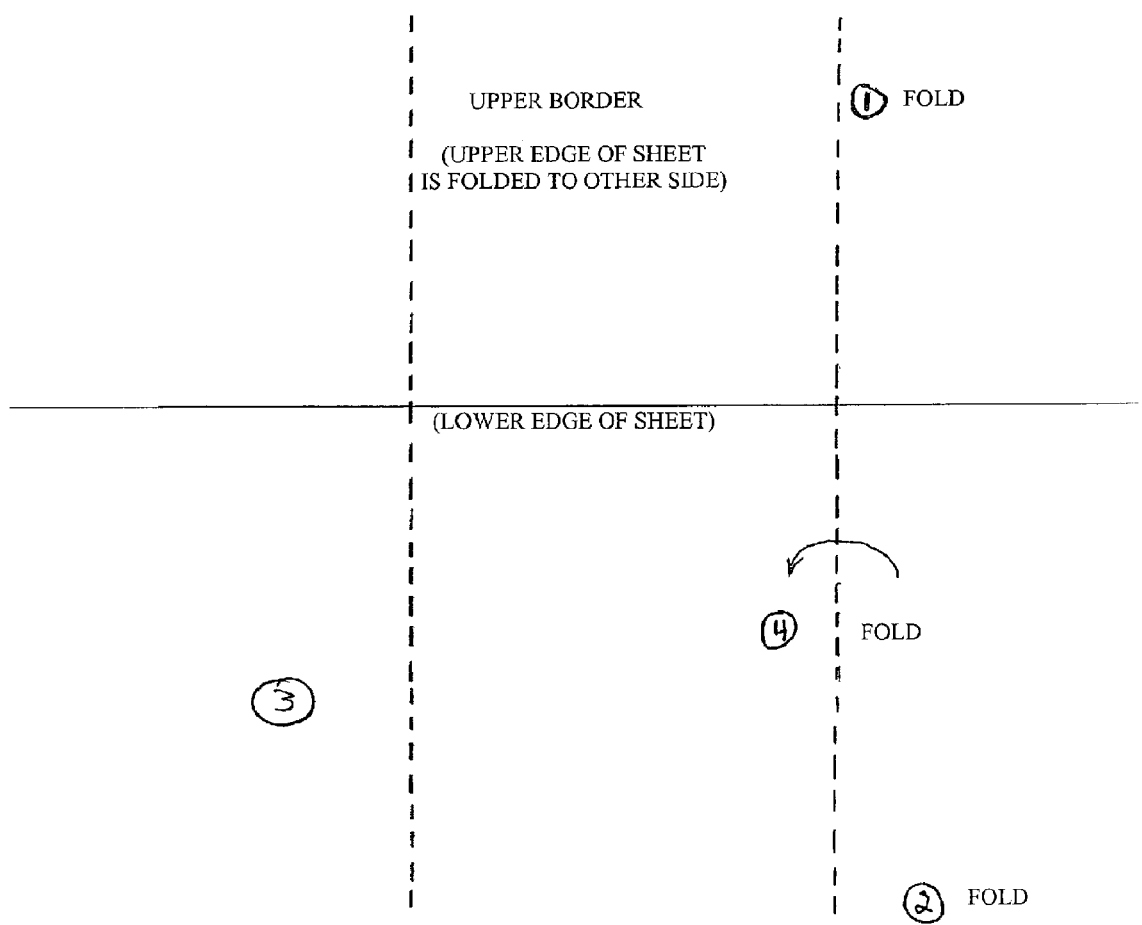
Figure 9C:
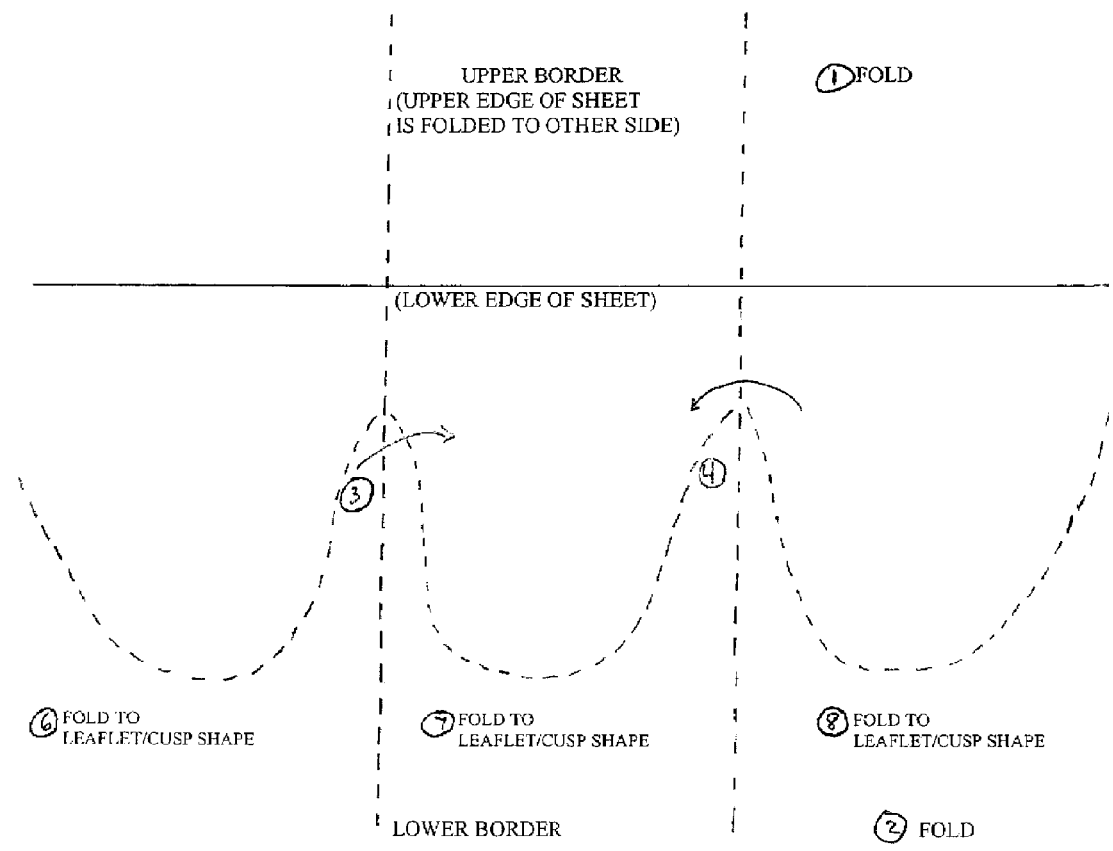

The cusp or leaflet portion 220 of the valve means 200 is formed by folding of the pericardium material used to create the valve. FIGS. 3A and 3B depict the way the sheet of heart valve starting material is folded. The starting material is preferably a flat dry sheet, which can be rectangular or other shaped. The cusps/leaflets 221, 222 and 223 open in response to blood flow in one direction and close in response to blood flow in the opposite direction. Preferably the cusp or leaflet portion 220 of the valve means 200 contains the same number of cusps as the native valve being replaced, in substantially the same size and configuration. FIGS. 9A-9C depict a preferred configuration for folds to create the leaflets/cusps. The leaflet forming portion is a single, continuous, uncut layer affixed to the interior of the cuff layer to form the leaflets/cusps, unlike prior efforts that have involved suturing of three separate leaflet/cusp portions onto the main valve body portion. The leaflets are formed from the free edge of the material after forming the cuff portion. Referring now to FIGS. 9-A, 9B, and 9C, with flat sheet on a table, a person facing the sheet would create a cuff at the upper border of sheet by folding the horizontal top edge away/downwardly (fold no. 1). The leaflet portion is formed by folding the sheet's lower half towards the folder/upwardly, as shown in FIG. 9A (fold no. 2). The sheet, now with the upper cuff and bottom inward fold, is folded inwardly at two preferably equidistant vertical points as shown in FIG. 9B to create the leaflet/cusp portion (folds nos. 3 and 4). The leaflets/cusps are formed by folding fold nos. 6, 7 and 8 after the two opposite vertical edges of sheet are joined to create a cylindrical valve shape, depicted in FIGS. 1 and 3B. The inner leaflet layer is preferably attached to the outer cuff layer by curved or straight continuous suturing. Although a preferred embodiment of the invention comprises a single piece of valve material folded to create the valve body and a leaflet-forming portion that has no cuts or sutures, the inventors have discovered that as long as the leaflet portion of the valve itself is formed from a single piece of biocompatible valve material, the other portions of the valve can be formed by suturing of one or more separate pieces of material without losing the novel and improved qualities of the present invention. This allows for the valve to be made even stronger, more durable and easier to make. This alternate embodiment comprises a leaflet forming layer made of a single piece of valve material attached to a separate piece forming the valve body having a folded cuff portion. The single piece leaflet forming layer is preferably cylindrical in shape and can be formed with or without folding. In this embodiment the single piece leaflet layer can itself be attached to the stent with or without a cylindrical cuff portion. Attachment is preferably by suturing, particularly continuous single or double sutures.

Method of Making Replacement Heart Valve Device

The present invention also comprises a method of making a replacement heart valve device. In order to make the valve, the biocompatible tissue material is isolated and all the fat tissue and extra fibers are removed. Cleaning is preferably accomplished by using a hydromechanical force-based cleaning device to separate tissue layers and hydration with distilled water to remove unwanted layers. Once the pericardium is completely clean, it is subjected to photo-mechanical compression, then the valve is formed and placed in sequential solutions of isopropyl alcohol of about 70-100%, ethanol of about 70-100%, glycerol and glutaraldehyde preferably at a concentration of about 0.07-25% for about 36 hours, respectively. The material is preferably photomechanically compressed to remove lipids and produce protein coagulation to make the surface smoother and more compact and biocompatible, decreasing the molecular distance of collagen fibers. The exposure to light and mechanical compression cause protein denaturation making the material stronger and more homogeneous and biocompatible. Gas sterilization can also be used to sterilize the tissue membrane material. The valve is formed by taking a flat sheet of the material and folding it in such a way that forms a three-leaflet or desired number of leaflet valve as shown in FIGS. 3A and 3B and/or FIGS. 9A, 9B and 9C. The folding of the pericardium material to create the cusps or leaflets reduces the extent of suturing otherwise required, and resembles the natural form and function of the valve leaflets. It also greatly reduces the risk of tearing of the cusps or leaflets, since they are integral to the valve rather than being attached by suturing.

In a preferred embodiment, the single continuous piece of membrane is folded inward to form an inner leaflet layer within the outer cuff. The single leaflet layer is then attached to the cuff layer to form valve cusps in one of three preferred ways: (i) by curved or straight continuous single or double sutures that affix and form the bases or recesses of the valve cusps; (ii) by lengthwise suture lines attaching the leaflet layer to the cuff layer with the bases or recesses of the valve cusps being thus formed of the folded edge of the membrane; (iii) by further folding of the membrane into lengthwise pleats secured by lengthwise suture attaching the leaflet layer to the cuff layer with the bases or recesses of the valve cusps being thus formed of the folded edge of the membrane, done for the purpose of giving greater strength and durability to the attachment points of the leaflet layer.

In order to make the pericardium material less slippery and easier to fold, the pericardium is dried, preferably with artificial light using a multi-watt lamp with the pericardium or other biocompatible membrane material placed in a flat aluminum surface to dry it homogeneously. A photomechanical drying machine can also be used. The final result is a homogeneous tissue that looks like plastic paper and makes it easy to manipulate to fold and suture the valve. Once the valve is formed, it is re-hydrated by placing it in a solution of water and 70% alcohol. In approximately 3 days the valve is fully rehydrated. The suturing of membrane layers to form the valve is done with single, double, or more continuous suture material. This form of suturing has great advantages for durability and avoidance of damage to the membrane and can be performed by sewing machines. The attachment points of the leaflet layer to the cuff layer may be reinforced by folding an additional layer of membrane over the attachment point before suturing, this layer being formed of a projected tab of the continuous piece of leaflet membrane. The free edge of the leaflet layer may be straight or curved, and this free edge forming the free edges of the individual leaflets may be contoured in parabolic or curved shape.

Attachment of the Valve Means to the Stent Member

The valve means 200 is then attached to the inner channel of the stent member 100 by suturing the outer surface of the valve means' pericardium material to the stent member. FIG. 7 depicts preferred suture points of one embodiment of the present invention: 3-point fixation or 6-point fixation at each border of the stent. Other fixation schemes can be utilized, such as, by way of non-limiting example, fixation on both borders 18 points at each end following a single plane and 36 fixation points following to adjacent vertical planes. The use of only one plane of fixation points helps prevent systolic collapse of the proximal edge of the valve means. A fold on the border of the pericardium material prevents tearing. The attachment position of the valve is preferably closer to the proximal and wider part of the stent.

The sequence of steps can vary. The pericardium material can be fixed in glutaraldehyde before attachment to the stent or the valve can be formed and then fixed with glutaraldehyde after mounting it in the stent. One observation noted is that the material becomes whiter and apparently increases its elasticity. 1 mm vascular clips keep the cusps coapted while fixing them in glutaraldehyde. The use of metallic clips to keep both cusps adjacent to each other after 24 hours of fixation in glutaraldehyde helps to educate the material and make the primary position of the valve cusps adjacent to each other. After the clips are removed, there are no lesions to the valve.

Different suture materials can be used, including, in a preferred embodiment, Prolene 1-0 to 8-0 and Mersilene 1-0 to 8-0 which is a braided suture.

Implantation of Replacement Heart Valve Device

The replacement heart valve device of the present invention is preferably used in surgical procedures involving the percutaneous and transluminal removal of the diseased or defective heart valve and the percutaneous and transluminal implantation of the new heart valve described above. The defective heart valve is removed by a suitable modality, such as, for example, laser, ultrasound, mechanical, or other suitable forms of delivery of energy, or phacoemulsion, including, but not limited to, laser lithotripsy, mechanical lithotripsy, electrohydraulic lithotripsy, and laser or mechanical ablation. To remove the native heart valve that is being replaced, a guidewire is inserted percutaneously and transluminally using standard vascular or angiography techniques. The distal end of the guidewire is manipulated to extend through and across the defective heart valve. Then a catheter is advanced distally through the femoral artery to a point proximal to the defective heart valve, between the origin of the coronary artery and the origin of the right subclavian artery. The position of the distal end of catheter can be monitored by observation of radiopaque markers. Collector member is preferably inflated and occludes the aorta at a point between the origin of the coronary artery and the right subclavian artery. Next, a balloon and cutting tool are advanced through the catheter so that the cutting tool and uninflated balloon are distal to the defective heart valve. Optionally an additional step, such as balloon dilatation or atherectomy, may be required to provide a passageway through the heart valve. A catheter is also placed into the coronary sinus via a transjugular puncture. This catheter is used for infusion of blood or cardioplegia solution during the portion of the procedure when the aorta is occluded. The absence of valves in the cardiac venous system allows retrograde flow so that there will be an effluence of fluid from the coronary arteries. This flow of fluid is desired to prevent embolization of material into the coronary arteries during the procedure. Once the cutting tool is in place, the balloon is inflated and flexible shaft is rotated. Once the cutting tool has reached the appropriate rotation speed, the cutting tool is pulled proximally to remove the defective heart valve. The balloon and the cutting tool are spaced apart so that the inflated balloon will be stopped by the perimeter, unremoved portion of the defective heart valve, which will signal the physician that the valve has been removed, as well as protect the heart and aorta from damage from the valve removal device. Once it is determined that the defective heart valve has been removed, the cutting tool is slowed or stopped altogether and the balloon is deflated. The cutting tool and the deflated balloon are pulled proximally through catheter. Then, a catheter containing an artificial heart valve is inserted and the artificial heart valve is placed as described above.

The delivery and implantation system of the replacement artificial heart valve of the present invention percutaneously and transluminally includes a flexible catheter 400 which may be inserted into a vessel of the patient and moved within that vessel as depicted in FIG. 8. The distal end 410 of the catheter 400, which is hollow and carries the replacement heart valve device of the present invention in its collapsed configuration, is guided to a site where it is desired to implant the replacement heart valve. The catheter has a pusher member 420 disposed within the catheter lumen 430 and extending from the proximal end 440 of the catheter to the hollow section at the distal end 410 of the catheter. Once the distal end 410 of the catheter is positioned as desired, the pusher mechanism 420 is activated and the distal portion of the replacement heart valve device is pushed out of the catheter and the stent member 100 partially expands. In this position the stent member 100 is restrained so that it doesn't pop out and is held for controlled release, with the potential that the replacement heart valve device can be recovered if there is a problem with the positioning. The catheter 400 is then retracted slightly and the replacement heart valve device is completely pushed out of the catheter 400 and released from the catheter to allow the stent member 100 to fully expand. If the stent member 100 preferably includes two circles of barbs on its outer surface as previously described, the first push and retraction will set one circle of barbs in adjacent tissue and the second push and release of the replacement heart valve device will set the other circle of barbs in adjacent tissue and securely fix the replacement heart valve device in place when the device is released from the catheter.

Alternatively, or in combination with the above, the replacement heart valve device could be positioned over a metallic guidewire that is advanced through the catheter. The replacement heart valve device of the present invention is preferably implanted percutaneously through an aortic passageway to, or near to, the location from which the natural heart valve has been removed. Referring to FIG. 8, the implantation system comprises a flexible hollow tube catheter 410 with a metallic guide wire 450 disposed within it. The stented valve device is collapsed over the tube and is covered by a moveable sheath 460. The moveable sheath 460 maintains the stented valve device in the collapsed position. The implantation method comprises the following steps: inserting the replacement heart valve device in the lumen of a central blood vessel via entry through the brachial or femoral artery using a needle or exposing the artery surgically; placing a guide wire 450 through the entry vessel and advancing it to the desired position; advancing dilators over the wire to increase the lumen of the entry site, thereby preparing the artery to receive the heart-valve; and advancing the heart-valve device to the desired place. The stented-valve device is released by pulling the cover sheath 460 of the delivery system allowing the self-expanding stent to achieve its full expansion. A balloon expandable stent can alternately be used to deliver the valve to its desired position. At this point, a pigtail catheter is advanced over the wire and an aortogram is performed to assess the competency of the valve.

Before creation of the valve means and implantation, the patient is studied to determine the architecture of the patient's heart. Useful techniques include fluoroscopy, transesophageal echocardiography, MRI, and angiography. The results of this study will enable the physician to determine the appropriate size for the replacement heart valve.

In one procedure for implantation of the replacement heart valve device of the present invention, the femoral artery of the patient is canulated using a Cook needle and a standard J wire is advanced into the artery either percutaneously or after surgical exposure of the artery. An 8 F introducer is advanced into the femoral artery over the wire. The J wire is then withdrawn and anticoagulation is started using heparin 60 U/Kg intravenously. Once vascular access is obtained an aortogram is performed for anatomical evaluation. A special wire (Lunderquist or Amplatz superstiff) is advanced into the aortic arch and dilators progressively larger are advanced over the wire, starting with 12 F all the way to 18 F. After this the valve introducer device containing the prosthetic valve device is then inserted and used to transport the replacement valve over a guidewire to the desired position. The stented-valve is released by pulling the cover sheath of the delivery system allowing the self-expanding stent to achieve its full expansion. At this point, a pigtail catheter is advanced over the wire and repeat aortogram is performed to assess the competency of the valve.

When the device is used to treat severe leakage of the aortic valve, the native valve is left in place and the prosthetic stented valve is deployed below the subclavian artery. When the device is used to treat aortic stenosis, first the stenotic valve needs to be opened using either aortic valvuloplasty or cutting and if this procedure induces aortic insufficiency the stented valve is placed to prevent the regurgitation.

Intravascular ultrasound or an angioscope passed intravascularly via either the venous system through the intra-atrial septum across the mitral valve and into the left ventricle or retrograde via the femoral artery would provide the added benefit of allowing constant high definition imaging of the entire procedure and high flow irrigation.

Once the endovascular implantation of the prosthetic valve device is completed in the host, the function of the prosthetic valve device can be monitored by the same methods as used to monitor valve replacements done by open heart surgery. Routine physical examination, periodic echocardiography or angiography can be performed. In contrast to open heart surgery, however, the host requires a short recovery period and can return home within one day of the endovascular procedure. The prosthetic valve device can be used in any patient where bioprosthetic valves are indicated, namely elderly patients with cardiac valve diseases, and patients unable to tolerate open heart procedures or life-long anticoagulation. In addition, with the development of longer-life, flexible, non-thrombogenic synthetic valve alternatives to bioprosthesis, the prosthetic valve device will be indicated in all patients where the relative advantages of the life-span, the non-thrombogenic quality, and the ease of insertion of prosthetic valve devices outweigh the disadvantages of mechanical valves. Anticoagulation may be beneficial in certain clinical situations for either short or long term use.

This method of percutaneous endovascular heart-valve replacement, in contrast to open heart surgical procedures, requires only local anesthesia, partial or no cardiac bypass, one to two days hospitalization, and should result in a reduced mortality rate as compared to open heart procedures.

While the present invention has been shown and described herein in what is considered to be a preferred embodiment thereof, illustrating the results and advantages over the prior art obtained through the present invention, the invention is not limited to the specific embodiments described above. Thus, the forms of the invention shown and described herein are to be taken as illustrative and other embodiments may be selected without departing from the spirit and scope of the present invention.

What is claimed is:

1. A percutaneously implantable replacement heart valve for implantation in a patient, comprising:
   a stent member having an inner channel, the stent member collapsible, expandable and configured for percutaneous delivery, wherein the stent member includes a tubular structure away from its central portion that flares at both ends in a trumpet-like configuration; and
   a valve means residing entirely within the inner channel of the stent member, the valve means including an outer cuff layer and two to four individual leaflets, wherein each of the two to four individual leaflets is rectangular in shape in side elevation view, wherein each of the two to four individual leaflets is bounded by lengthwise-oriented lines of sutures, wherein a crease is located between the two to four individual leaflets and the outer cuff layer at a base of the two to four individual leaflets, and wherein after implantation in the patient, the valve means resides as a single element entirely within the inner channel of the stent member, and wherein only the two to four individual leaflets reside radially inward from the outer cuff layer.

2. The percutaneously implantable replacement heart valve of claim 1, wherein the outer cuff layer and the two to four individual leaflets comprise a single continuous sheet of material.

3. The percutaneously implantable replacement heart valve of claim 1, wherein the outer cuff layer and the two to four individual leaflets are made of a biocompatible material.

4. The percutaneously implantable replacement heart valve of claim 3, wherein the biocompatible material comprises a treated pericardium tissue.

5. The percutaneously implantable replacement heart valve of claim 3, wherein the biocompatible material comprises a synthetic material.

* * * * *

UNITED STATES PATENT AND TRADEMARK OFFICE
CERTIFICATE OF CORRECTION

Page 1 of 1

PATENT NO.      : 8,790,398 B2
APPLICATION NO. : 14/136516
DATED           : July 29, 2014
INVENTOR(S)     : David Paniagua and R. David Fish It is certified that error appears in the above-identified patent and that said Letters Patent is hereby corrected as shown below:

Title Page, item [63] "Related U.S. Application Data" should appear as:

(63) Continuation of application No. 13/675,665, filed on Nov. 13, 2012, which is a continuation of application No. 10/887,688, filed on Jul. 10, 2004, now Pat. No. 8,308,797, which is a continuation-in-part of application No. 10/037,266, filed on Jan. 4, 2002, now abandoned.

Signed and Sealed this
Twenty-first Day of October, 2014

Michelle K. Lee
*Deputy Director of the United States Patent and Trademark Office*